US011872340B2

(12) United States Patent
Kleiner

(10) Patent No.: US 11,872,340 B2
(45) Date of Patent: Jan. 16, 2024

(54) ENDOLUMINAL VACUUM THERAPY DEVICE

(71) Applicant: Daniel Eduard Kleiner, Roxbury, CT (US)

(72) Inventor: Daniel Eduard Kleiner, Roxbury, CT (US)

(*) Notice: Subject to any disclaimer, the term of this patent is extended or adjusted under 35 U.S.C. 154(b) by 1055 days.

(21) Appl. No.: 16/516,881

(22) Filed: Jul. 19, 2019

(65) Prior Publication Data

US 2020/0009303 A1  Jan. 9, 2020

Related U.S. Application Data

(63) Continuation of application No. 14/405,110, filed as application No. PCT/AU2013/000262 on Mar. 15, 2013, now Pat. No. 10,369,259.

(Continued)

(51) Int. Cl.
*A61M 1/00* (2006.01)
*A61F 13/00* (2006.01)

(52) U.S. Cl.
CPC .............. *A61M 1/916* (2021.05); *A61M 1/77* (2021.05); *A61M 1/84* (2021.05); *A61M 1/915* (2021.05);
(Continued)

(58) Field of Classification Search
CPC .. A61M 1/0088; A61M 1/0023; A61M 1/008; A61M 1/0084; A61M 2210/106; A61M 2210/1064; A61F 13/0068
(Continued)

(56) References Cited

U.S. PATENT DOCUMENTS 3,753,439 A * 8/1973 Brugarolas ........... A61M 27/00
604/43
3,935,863 A 2/1976 Kliger
(Continued)

FOREIGN PATENT DOCUMENTS

DE  102010053888  1/2012
EP  1572286  9/2005
(Continued)

OTHER PUBLICATIONS

Extended European Search Report, European Patent Application No. 13800697.8, dated Jan. 7, 2016, 5 pages.
(Continued)

*Primary Examiner* — Andrew J Mensh
(74) *Attorney, Agent, or Firm* — Fitch Even Tabin & Flannery LLP

(57) ABSTRACT

There are provided devices for applying negative pressure to a wound in an endoluminal surface of a patient to facilitate healing of the wound and methods for use of the devices. The device (69, 94, 134, 140, 156, 164) comprises a flexible porous element with an outer face defined between opposite proximal and distal ends of the porous element. A suction tube (30) for being connected to a suction source externally of the patient's body is in fluid communication with the porous element (14) to apply the negative pressure to the wound via the outer face of the porous element. In some embodiments, the porous element has a longitudinal passageway (16) for passage of bodily substances of the patient along the lumen defining the endoluminal surface through the porous element. In such embodiments, the device may also have at least one absorbent element (70, 80) for absorbing the bodily substances and which is disposed forwardly or rearwardly of the porous element (14). Embodiments of the device may also include a drainage tube (22) for collection and drainage of bodily substances from (Continued)

the patient and which is received in the longitudinal passageway (16) of the porous element. In other embodiments, the porous element can be in the form of a mat wrapped around a feeding or other insertion tube. The porous element of a device embodied by the invention may also include one or more irrigation channels (85, 86) for delivery of an irrigation fluid into or though, the porous element. The porous element and/or absorbent element(s) may be sponge(s).

23 Claims, 17 Drawing Sheets

Related U.S. Application Data

(60) Provisional application No. 61/655,238, filed on Jun. 4, 2012, provisional application No. 61/654,909, filed on Jun. 3, 2012.

(52) U.S. Cl.
CPC .......... *A61F 13/00068* (2013.01); *A61M 1/85* (2021.05); *A61M 1/92* (2021.05); *A61M 2210/106* (2013.01); *A61M 2210/1064* (2013.01)

(58) Field of Classification Search
USPC .......................................................... 604/543
See application file for complete search history.

(56) References Cited

U.S. PATENT DOCUMENTS

| | | | |
|---|---|---|---|
| 4,523,920 A | 6/1985 | Russo | |
| 4,525,166 A | 6/1985 | Leclerc | |
| 4,533,352 A * | 8/1985 | Van Beek | A61G 13/102 |
| | | | 604/313 |
| 5,045,075 A | 9/1991 | Ersek | |
| 5,261,893 A | 11/1993 | Zamierowski | |
| 5,324,306 A | 6/1994 | Makower | |
| 5,437,651 A | 8/1995 | Todd | |
| 5,599,330 A | 2/1997 | Rainin | |
| 5,628,735 A | 5/1997 | Skow | |
| 5,636,643 A | 6/1997 | Argenta | |
| 5,769,882 A * | 6/1998 | Fogarty | A61F 2/07 |
| | | | 623/1.21 |
| 6,123,697 A * | 9/2000 | Shippert | A61B 17/12104 |
| | | | 604/514 |
| 6,132,415 A | 10/2000 | Finch | |
| 6,174,306 B1 | 1/2001 | Fleischmann | |
| 6,235,009 B1 | 5/2001 | Skow | |
| 6,420,622 B1 | 7/2002 | Johnston | |
| 6,695,823 B1 | 2/2004 | Lina | |
| 6,767,334 B1 | 7/2004 | Randolph | |
| 7,125,402 B1 | 10/2006 | Yarger | |
| 7,144,390 B1 | 12/2006 | Hannigan | |
| 7,182,758 B2 | 2/2007 | McCraw | |
| 7,381,859 B2 | 6/2008 | Hunt | |
| 7,438,705 B2 | 10/2008 | Karpowicz | |
| 7,678,102 B1 | 3/2010 | Heaton | |
| 7,731,702 B2 | 6/2010 | Bybordi | |
| 7,763,769 B2 | 7/2010 | Johnson | |
| 7,981,098 B2 | 7/2011 | Boehringer | |
| 8,007,541 B2 | 8/2011 | Benz | |
| 8,715,267 B2 | 5/2014 | Bengtson | |
| 2002/0016577 A1 | 2/2002 | Ohmstede | |
| 2002/0082567 A1 | 6/2002 | Lockwood | |
| 2002/0115952 A1 | 8/2002 | Johnson | |
| 2003/0040687 A1 | 2/2003 | Boynton | |
| 2004/0030304 A1 | 2/2004 | Hunt | |
| 2004/0054338 A1 | 3/2004 | Bybordi | |
| 2004/0127862 A1 | 7/2004 | Bubb | |
| 2004/0138758 A1 | 7/2004 | Evans | |
| 2004/0243073 A1 | 12/2004 | Lockwood | |
| 2005/0004534 A1 | 1/2005 | Lockwood | |
| 2005/0085795 A1 | 4/2005 | Lockwood | |
| 2005/0101940 A1 | 5/2005 | Radl | |
| 2005/0119617 A1 | 6/2005 | Stecker | |
| 2005/0137539 A1 | 6/2005 | Biggie | |
| 2005/0148913 A1 | 7/2005 | Weston | |
| 2005/0186260 A1 | 8/2005 | Narini | |
| 2005/0222544 A1 | 10/2005 | Weston | |
| 2005/0273066 A1 | 12/2005 | Wittmann | |
| 2006/0036221 A1 | 2/2006 | Watson, Jr. | |
| 2006/0041247 A1 | 2/2006 | Petrosenko | |
| 2006/0129137 A1 | 6/2006 | Lockwood | |
| 2006/0142736 A1 | 6/2006 | Hissink | |
| 2007/0005004 A1 | 1/2007 | Hynes | |
| 2007/0032754 A1 | 2/2007 | Walsh | |
| 2007/0055209 A1 | 3/2007 | Patel | |
| 2007/0129660 A1 | 6/2007 | McLeod | |
| 2007/0167926 A1 | 7/2007 | Blott | |
| 2007/0219585 A1 | 9/2007 | Cornet | |
| 2007/0282309 A1 | 12/2007 | Bengtson | |
| 2007/0282310 A1 | 12/2007 | Bengtson | |
| 2008/0004559 A1 | 1/2008 | Riesinger | |
| 2008/0009812 A1 | 1/2008 | Riesinger | |
| 2008/0082059 A1 | 4/2008 | Fink | |
| 2008/0119802 A1 | 5/2008 | Riesinger | |
| 2008/0161778 A1 | 7/2008 | Steward | |
| 2008/0228153 A1 | 9/2008 | Shacham | |
| 2008/0243096 A1 | 10/2008 | Svedman | |
| 2008/0281281 A1 | 11/2008 | Meyer | |
| 2008/0294147 A1 | 11/2008 | Radl | |
| 2008/0300578 A1 | 12/2008 | Freedman | |
| 2009/0005762 A1 | 1/2009 | Nishtala | |
| 2009/0012501 A1 | 1/2009 | Boehringer | |
| 2009/0192499 A1 | 7/2009 | Weston | |
| 2009/0220577 A1 | 9/2009 | Hierlemann | |
| 2009/0234306 A1 | 9/2009 | Vitaris | |
| 2010/0063464 A1 | 3/2010 | Meyer | |
| 2010/0168691 A1 | 7/2010 | Long | |
| 2010/0262126 A1 | 10/2010 | Hu | |
| 2011/0028919 A1 | 2/2011 | Johnnison | |
| 2011/0028920 A1 | 2/2011 | Johnnison | |
| 2011/0060204 A1 | 3/2011 | Weston | |
| 2011/0112492 A1 | 5/2011 | Bharti | |
| 2012/0123359 A1 * | 5/2012 | Reed | A61M 1/784 |
| | | | 604/319 |
| 2013/0023840 A1 * | 1/2013 | Loske | A61B 90/39 |
| | | | 604/319 |

FOREIGN PATENT DOCUMENTS

| | | |
|---|---|---|
| GB | 1534677 | 12/1978 |
| GB | 2356148 | 5/2001 |
| WO | 1993009727 | 5/1993 |
| WO | 2001085228 | 11/2001 |
| WO | 2003028786 | 4/2003 |
| WO | 2007015964 | 2/2007 |
| WO | 2007030598 | 3/2007 |
| WO | 2007030599 | 3/2007 |
| WO | 2007030601 | 3/2007 |
| WO | 2009114786 | 9/2009 |
| WO | 2009114790 | 9/2009 |
| WO | 2009117635 | 9/2009 |
| WO | 2010063466 | 6/2010 |
| WO | 2010080667 | 7/2010 |
| WO | 2012071626 | 6/2012 |
| WO | 2012123414 | 9/2012 |

OTHER PUBLICATIONS

International Search Report and Written Opinion, International Patent Application No. PCT/AU2013/000262, dated Jun. 26, 2013, 17 pages.

\* cited by examiner

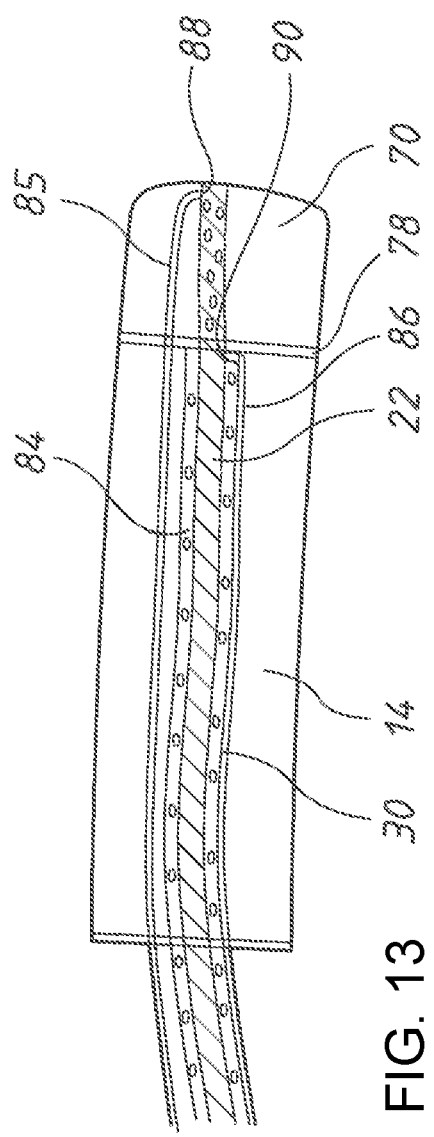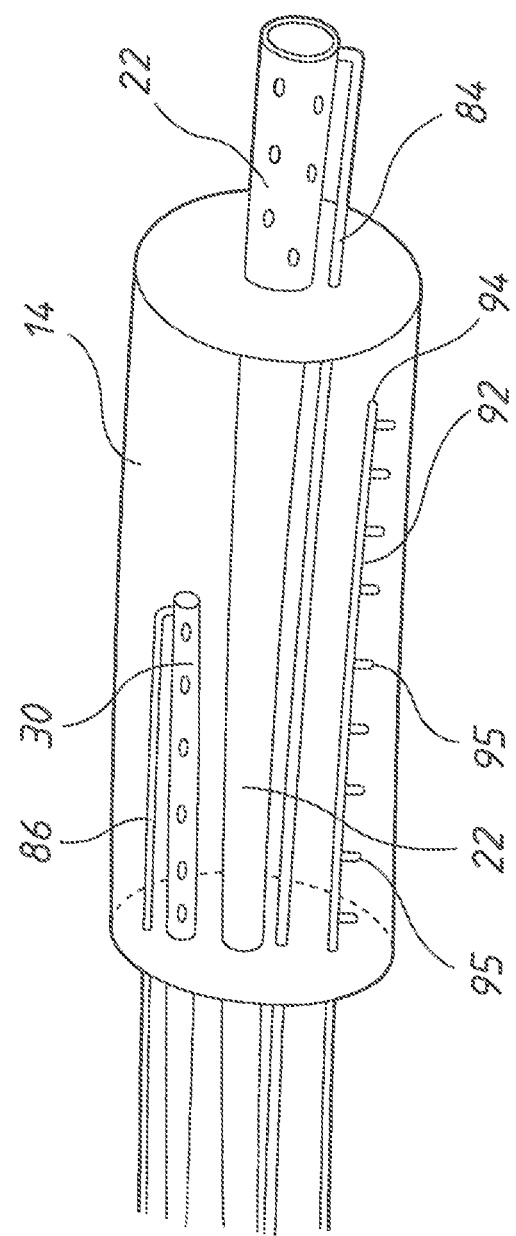
FIG. 13
FIG. 14

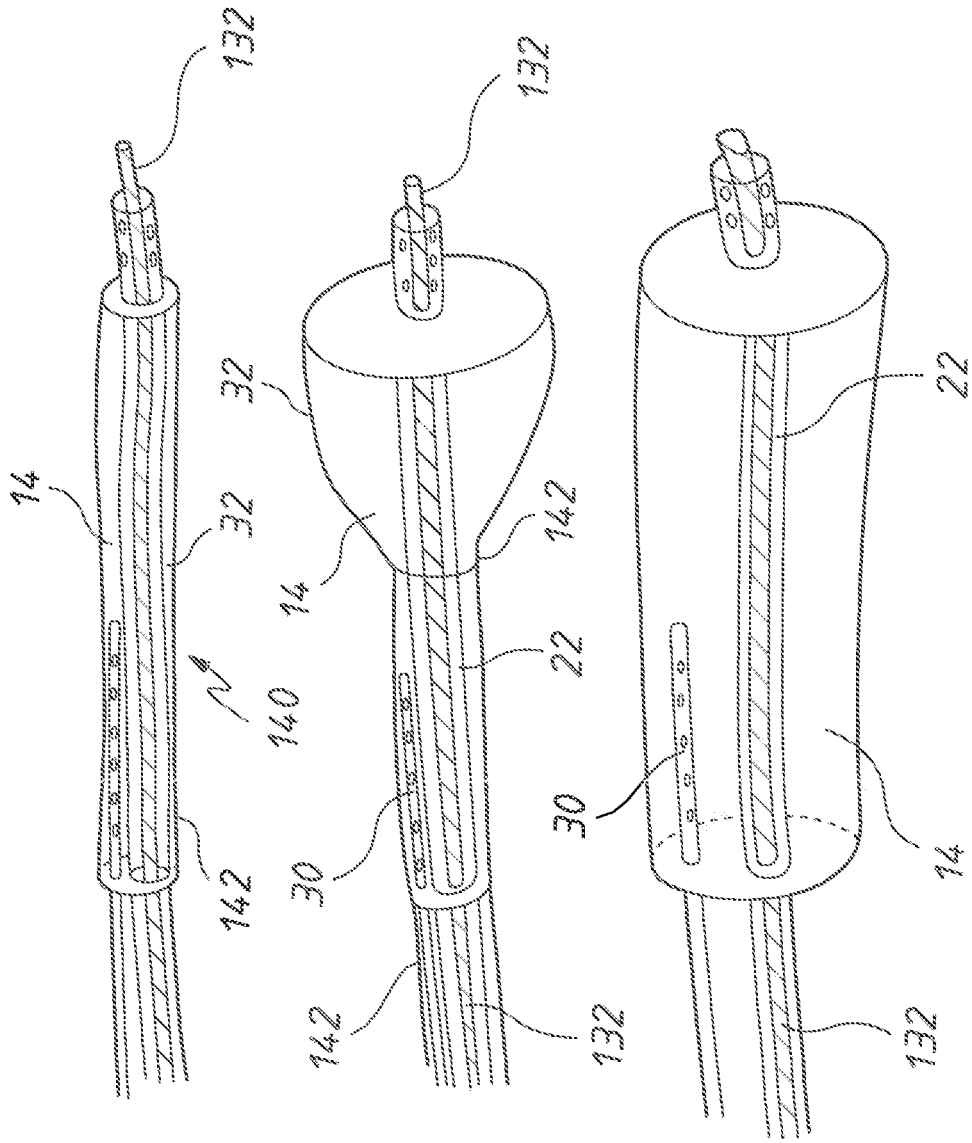

ENDOLUMINAL VACUUM THERAPY DEVICE

CROSS-REFERENCE TO RELATED APPLICATIONS

This application is a continuation of U.S. patent application Ser. No. 14/405,110, filed Dec. 2, 2014, which is a national phase entry of PCT/AU2013/000262, filed Mar. 15, 2013, which claims the benefit of 35 U.S.C. § 119 based on the priority of U.S. Provisional Application No. 61/655,238, filed Jun. 4, 2012, and U.S. Provisional Application No. 61/654,909, filed Jun. 3, 2012, all of which are hereby incorporated by reference in their entireties.

FIELD OF THE INVENTION

The invention relates to a device for facilitating healing of a wound in an endoluminal surface of a patient and methods for use of the device.

BACKGROUND OF THE INVENTION

Cancer remains one of the major modern day health issues and accounts for a large proportion of health and hospital costs. For example, in excess of 106,000 new cases of large bowel cancer are diagnosed each year in the United States alone. Of these, about 65,230 cases are colon cancer while the remainder of patients have cancer of the rectum. In the United States, approximately 49,920 people die from colorectal cancer (CRC) yearly, with about 1 in 17 people developing CRC during some stage of their life.

Surgery is the mainstay of care for CRC. Radiotherapy (for rectal cancer) and/or chemotherapy can also be administered. About 60% of rectal cancer patients have surgery as well as both radiotherapy and chemotherapy. Surgery involves resection of the affected region and rejoining of the bowel forming an anastomosis. Commonly, a colostomy involving attaching the top end of the colon to an opening (known as a stoma) made in the abdomen is performed to divert faecal matter away from the anastomosis to a collection bag arranged externally of the patient's body while the anastomosis is healing. Connection of the lower end of the small intestine (the ileum) to the stoma is known as an ileostomy. The colostomy or ileostomy is usually temporary requiring a subsequent reversal operation to be performed.

A patient who has a rectal cancer, for example, may have a Lower Anterior Resection (LAR). Of such patients in the United States, about 32% will undergo a temporary diverting loop ileostomy. A patient that has an LAR but not an ileostomy has a 10-30% risk of having an anastomotic leak which can be either symptomatic (10-15%) or asymptomatic. However, patients that suffer anastomotic leakage not only then require an ileostomy, an abscess can form at the site of the leakage which then requires drainage, involving a yet further operation complicating the healing process. If the leakage is symptomatic the mortality rate is 6-22%.

The average time to surgical reversal of a colostomy or ileostomy is about 15 to 23 weeks. Immediately prior to the reversal, a contrast (e.g., barium) enema is performed to ensure that the anastomosis has healed. A routine reversal is not without its own risks, with the overall complication rate (e.g., wound infection etc) estimated at about 19.8%. About 3% of patients suffer an anastomotic leak associated with the reversal operation. Moreover, in the United States, the financial cost for the colostomy or ileostomy and subsequent reversal can be US$10,000 to $15,000 or more per patient.

As such, not only is there significant morbidity and mortality associated with anastomotic leakage arising from primary surgery for treatment of CRC, the risk of leakage is compounded by subsequent diverting colostomy/ileostomy procedures and reversal operations where performed, the latter treatments adding significantly to the financial burden involved in obtaining treatment.

The application of sub-atmospheric pressure to acute or chronic wounds to promote wound healing is known as negative pressure wound therapy (NPWT) or vacuum assisted closure (VAC). VAC therapy involves creating a negative-pressure in the local wound environment, drawing away bacteria, exudate, fluid and desiccated tissue from the wound site. Besides improving localised conditions and reducing oedema for wound healing, the negative pressure may draw wound edges together and increase the rate of healing by promoting blood flow and facilitating localised cell migration and proliferation. Indeed, it is believed VAC therapy can increase the rate of wound closure.

Conventionally, VAC therapy has been applied to wounds in the skin such as burns, grafts, surgical incisions, diabetic ulcers, pressure ulcers, venous stasis ulcers and wounds arising from trauma. These "wound VAC" devices comprise a pad of open-cell sponge like material or a porous mat for being placed on the wound. A vacuum is applied to the sponge via a drainage tube through which fluid and exudate from the wound that is drawn into the sponge or mat is drained away. A drape can be laid over the sponge or porous mat to facilitate sealing of the wound. Such devices are commercially available and, for example, are described in U.S. patent application Ser. Nos. 11/186,056, 11/347,073, 11/409,116, 11/268,212, 12/233,211, and International Patent Application WO 93/09727. In more recent times, VAC devices comprising like porous sponges and mats have been used to drain seromas and fluids from internal bodily spaces following surgery and to facilitate the healing of wounds on outer surfaces of internal body organs and tissues, examples of which are described in WO 03/028786, U.S. Pat. No. 5,437,651 and U.S. patent application Ser. No. 11/646,918.

SUMMARY OF THE INVENTION

Broadly stated, the present invention relates to the provision and use of a vacuum assisted closure (VAC) type device to facilitate the healing of a wound in the body of a patient. Whilst, at least some forms, devices embodied by the invention have application in the treatment of anastomotic wounds resulting from surgery such as for colorectal cancer (CRC), the invention is not limited thereto.

In one aspect of the invention there is provided a device for applying a negative pressure to an endoluminal surface in the body of a patient to treat a wound in the endoluminal surface, comprising:

a flexible porous element with a peripheral outer face defined between opposite proximal and distal ends of the porous element;

at least one absorbent element for absorbing bodily substances within a bodily lumen formed by the endoluminal surface and which is disposed forwardly or rearwardly of the porous element, a respective juncture being defined between the porous element and the absorbent element; and a suction tube for being connected to a suction source externally of the patient's body and which is in fluid communication with the porous element to apply the negative pressure to the wound via the outer face of the porous element upon operation of the suction source, at least one longitudinally extending through passageway of the porous element extending into the absorbent element through the juncture between the porous element and the absorbent element for passage of the bodily substances from the lumen formed by the endoluminal surface through the device, and the juncture being otherwise adapted against egress of the bodily substances between the porous element and the absorbent element.

Typically, the through passageway of the porous element extends entirely through the respective said absorbent element.

Typically, the device further comprises a drainage tube for collection and drainage of the bodily substances from the patient, wherein the drainage tube is received in the through passageway of the porous element.

In at least some embodiments, the device further comprises at least one irrigation channel for delivery of an irrigation fluid into, or through, the porous element.

In another aspect of the invention there is provided a device for applying a negative pressure to an endoluminal surface in the body of a patient to treat a wound in the endoluminal surface, comprising:
- a flexible porous element with a peripheral outer face for contact with the wound, the outer face being defined between opposite proximal and distal ends of the porous element, and the porous element having at least one through passageway extending from its said proximal end to its distal end for passage of bodily substances through the porous element from a lumen defined by the endoluminal surface;
- a suction tube for being connected to a suction source externally of the patient's body and which is in fluid communication with the porous element to apply the negative pressure to the wound via the outer face of the porous element upon operation of the suction source; and
- at least one irrigation channel for delivery of an irrigation fluid into, or through, the porous element.

Typically, a device according to this aspect of the invention further comprises an irrigation channel for delivery of the irrigation fluid to one or more of the suction tube, an outer peripheral region of the porous element adjacent the outer face of the porous element, and a drainage tube disposed in the through passageway of the porous element.

In another aspect of the invention there is provided a device for applying a negative pressure to a wound in the skin of a patient, comprising:
- an insertion tube for being inserted into the wound;
- a flexible porous element for being inserted into the wound such that the porous element is pressed against the wound for application of the negative pressure to the wound; and
- a suction tube for being connected to a suction source externally of the patient's body and which is in fluid communication with the porous element to apply the negative pressure to the porous element with operation of the suction source, the porous element being mounted on the insertion tube.

Typically, the insertion tube passes through the porous element.

In at least some embodiments, the porous element is in the form of a mat for being wrapped around the insertion tube. In this instance, the device can include a fastening system for fastening the mat when wrapped around the tube to retain the mat in a wrapped condition.

The insertion tube can be provided with an inflatable balloon for being inflated in a lumen of the patient.

In another aspect of the invention there is provided a device for applying a negative pressure to an endoluminal surface in the body of a patient to treat a wound in the endoluminal surface, comprising:
- a flexible porous element with a peripheral outer face defined between opposite proximal and distal ends of the porous element;
- a suction tube for being connected to a suction source externally of the patient's body and which is in fluid communication with the porous element to apply the negative pressure to the wound via the outer face of the porous element upon operation of the suction source, the porous element having at least one through passageway extending from its proximal end to its distal end; and
- a feeding tube inserted through the through passageway of the porous element.

Typically, the feeding tube includes a longitudinal drainage lumen for drainage of bodily substances in a lumen defined by the endoluminal surface through the porous element, and a longitudinal feeding lumen which opens into the lumen of the patient for facilitating feeding and/or hydration of the patient.

In at least some embodiments, the feeding tube has an inflatable balloon provided on a proximal end region of the feeding tube.

In another aspect of the invention there is provided a method for treating a wound in an endoluminal surface in the body of a patient, comprising:
- providing a device for applying the negative pressure to the wound, the device having a flexible porous element with a peripheral outer face for contact with the wound and which is defined between opposite proximal and distal ends of the porous element, at least one absorbent element for absorbing bodily substances within a bodily lumen formed by the endoluminal surface and which is disposed forwardly or rearwardly of the porous element, a respective juncture being defined between the porous element and the absorbent element, and a suction tube for being connected to a suction source externally of the patient's body and which is in fluid communication with the porous element to apply the negative pressure to the wound via the outer face of the porous element upon operation of the suction source;
- locating the device in position in the lumen formed by the endoluminal surface; and
- applying the negative pressure to the wound via the outer face of the porous element, at least one longitudinally extending through passageway of the porous element extending into the absorbent element through the juncture between the porous element and the absorbent element for passage of the bodily substances from the lumen through the device, the juncture being otherwise adapted against egress of the bodily substances between the porous element and the absorbent element.

In another aspect of the invention there is provided a method for treating a patient with a wound in an endoluminal surface, comprising:
- providing a device for applying a negative pressure to the wound, the device comprising a flexible porous element with a peripheral outer face defined between proximal and distal ends of the porous element, and a suction tube for being connected to a suction source externally of the patient's body, the suction tube being in fluid communication with the porous element to apply the negative pressure to the outer face of the porous element upon operation of the suction source;

locating the device in position in a lumen defined by the endoluminal surface;

applying the negative pressure to the wound via the outer face of the porous element to treat the wound, the porous element having a through passageway extending from the distal to the proximal end of the porous element; and feeding and/or hydrating the patient utilising a feeding tube passing through the passageway of the porous element whilst the device is in position in the lumen.

In another aspect of the invention there is provided a method of providing a device for applying a negative pressure to a wound in the skin of a patient, comprising:

providing an insertion tube for being inserted though the wound into a lumen defined by an endoluminal surface of the patient;

providing a flexible porous element having a peripheral outer face defined between opposite proximal and distal ends of the porous element, the porous element being adapted to be inserted into the wound and connected to a suction source for application of the negative pressure to the outer face of the porous element; and mounting the porous element on the insertion tube for pressed contact of the outer face of the porous element with the wound when the insertion tube is inserted into the lumen of the patient.

In another aspect of the invention there is provided a method for treating a wound in the skin of a patient about an insertion tube passing through the wound into a lumen of the patient, comprising:

locating a flexible porous element mounted on the insertion tube into the wound, the porous element having a peripheral outer face defined between proximal and distal ends of the porous element, and the porous element being in fluid communication with a suction source externally of the patient's body for application of a negative pressure to the porous element; and applying the negative pressure to the wound via the outer face of the porous element.

Besides wounds arising from surgical resection, wounds that may be treated using devices embodied by the invention include those arising from diseases and physiological conditions, ablation, radiotherapy, chemotherapy or other medical treatments, and injuries due to accidents and trauma. Although at least some embodiments are particularly suitable for use in facilitating healing of an anastomotic or other wound in the endoluminal surface of the large bowel of the gastrointestinal (G.I) tract, devices in accordance with the invention may have application in other luminal structures such as those may be explored with an endoscope or similar type of viewing device. In particular, in at least some embodiments, a device embodied by the invention can be mounted on an endoscope and located in position within the lumen with the use of the endoscope (or other suitable insertion or viewing device). A guide wire can also be inserted along the relevant lumen, a device embodied by the invention moved along the guide wire into position, and the guide wire then withdrawn leaving the device behind within the relevant bodily lumen. This can be done under e.g., ultrasound or fluoroscopic guidance.

At least some embodiments in accordance with the invention are adapted for enabling bodily substances present within a bodily lumen in which the device is located to be diverted through the device whilst the device maintains suction on the wound. By allowing bodily substances present in the lumen to pass through the device whilst in position such as following surgery on the large bowel, the need for a diverting colostomy or ileostomy following resection of tissue for treatment of CRC may in at least some instances be reduced or avoided altogether. By avoiding or reducing the need for a colostomy or ileostomy, not only may the significant financial burden associated with patient treatment be lessened, patient psychological stress and discomfort stemming from the need for the patient to wear a waste collection bag into which bodily waste is received via the stoma is also avoided.

The use of a device as described herein may in one or more embodiments of the invention increase the rate of healing of the wound in the endoluminal surface of the patient. The risk of anastomotic leakage and associated morbidity and mortality may also be reduced in patients following surgery such as an LAR on whom a diverting loop ileostomy is not performed.

The term "bodily substances" as used herein is to be taken to encompass air, gases, fluids, mucous and waste bodily products (e.g., faecal matter) that may be present within the relevant lumen of the patient.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers, integers or steps.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed in Australia or elsewhere before the priority date of this application.

The features and advantages of the invention will become further apparent from the following detailed description of embodiments thereof together with the accompanying drawings. At least some like components of different embodiments of devices of the invention are numbered the same for convenience in the following description.

BRIEF DESCRIPTION OF THE ACCOMPANYING DRAWINGS

FIG. 13 is a diagrammatic view of another endoVAC device embodied by the invention;

FIG. 14 is a diagrammatic view of another endoVAC device embodied by the invention;

Figure 20A:
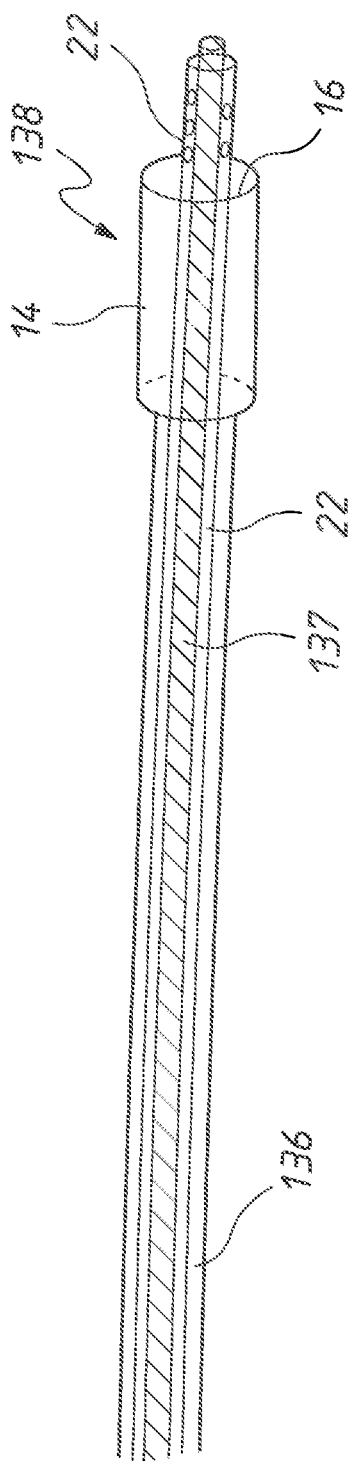
Figure 20B:
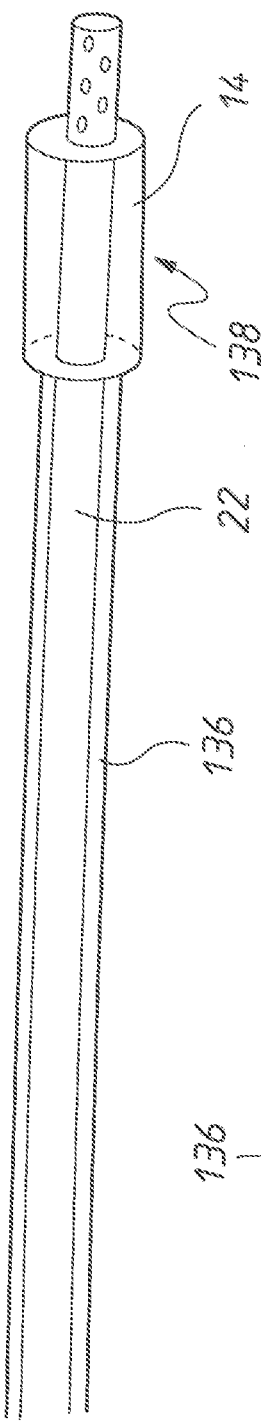
Figure 20C:
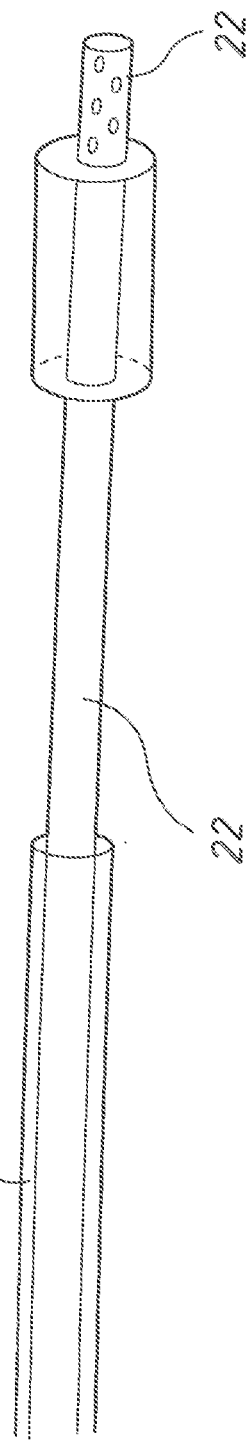
Figure 22:
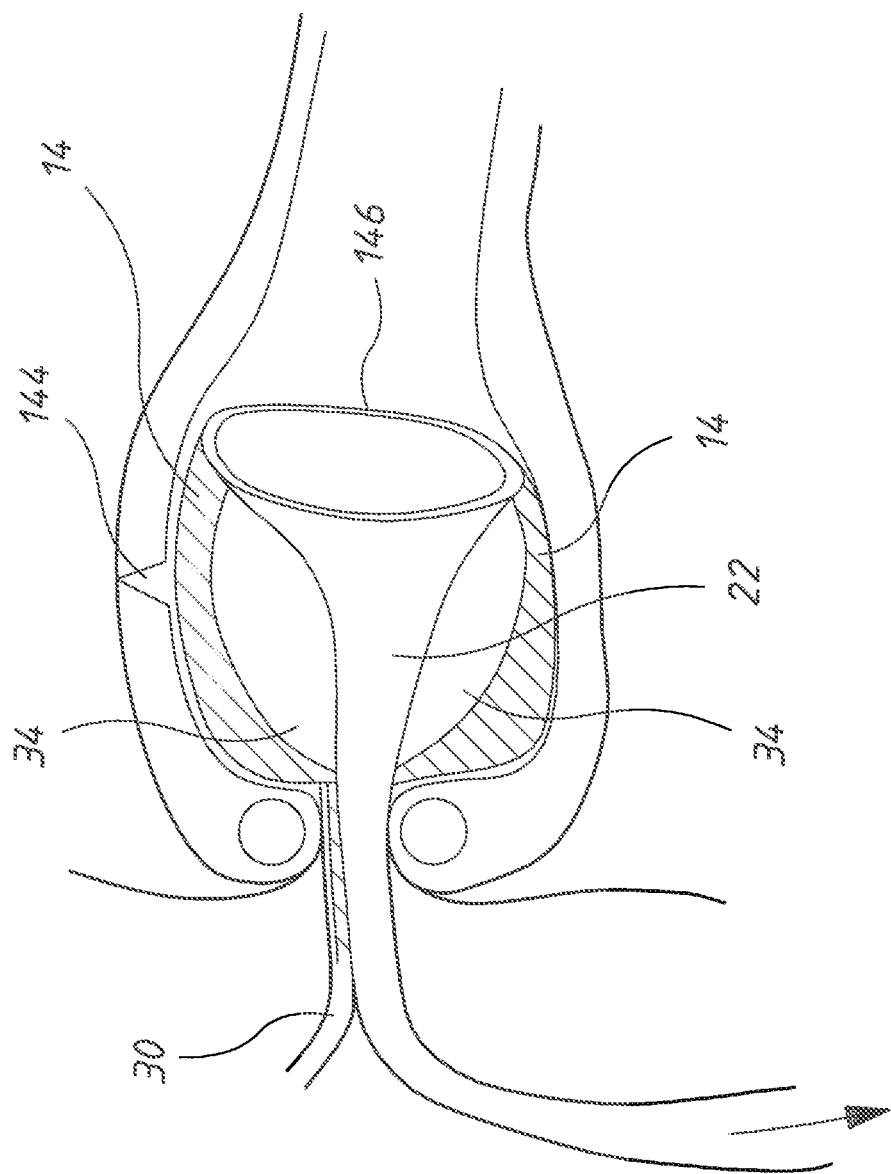
Figure 23:
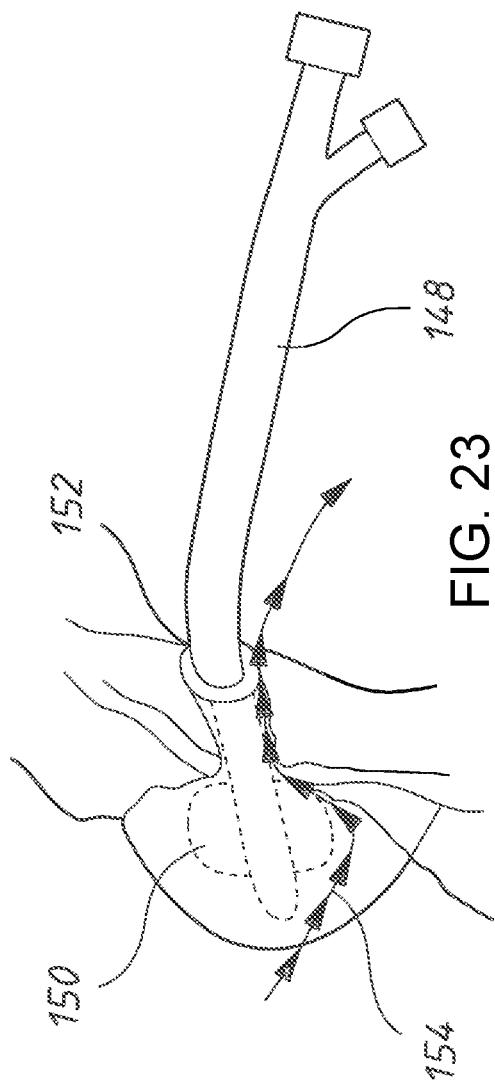
Figure 24:
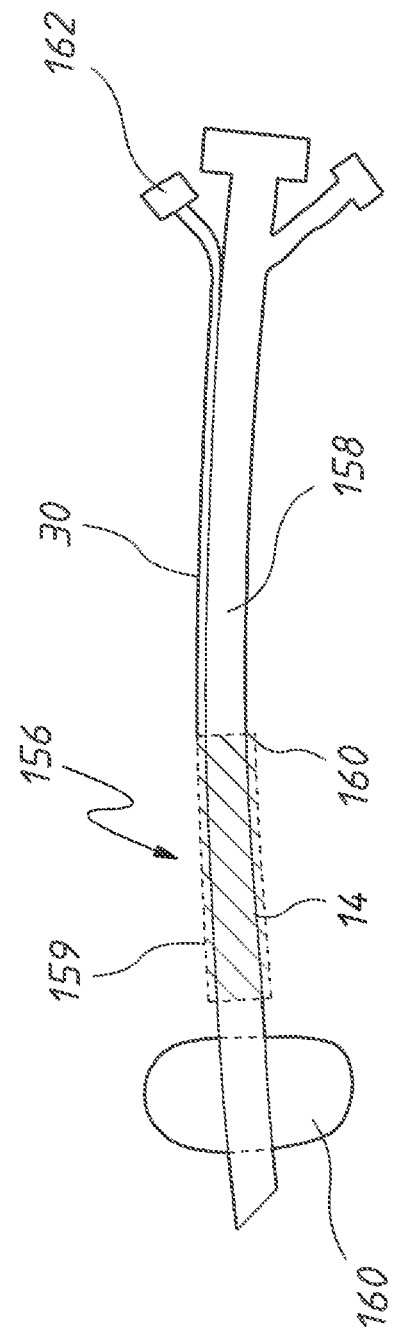
Figure 25A:
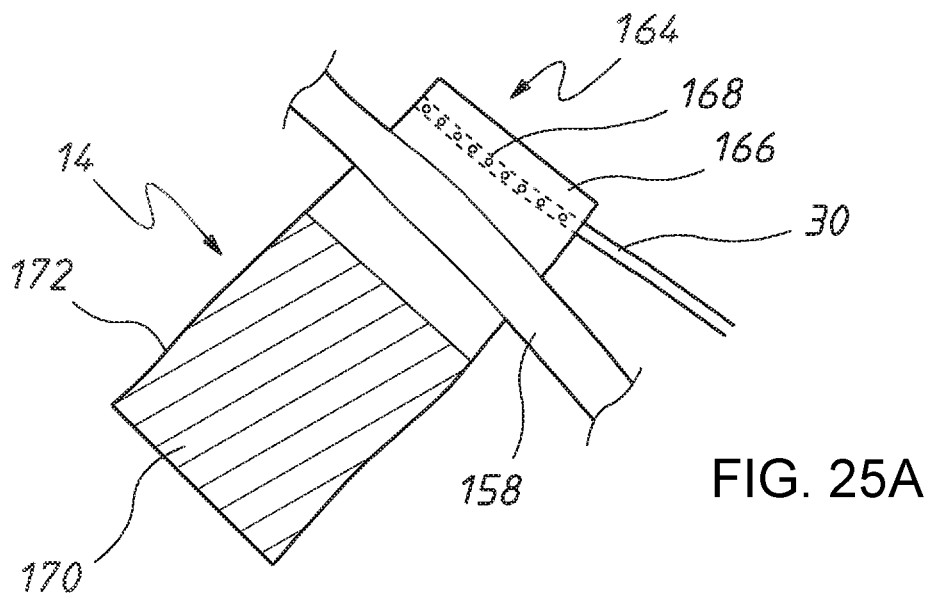
Figure 25B:
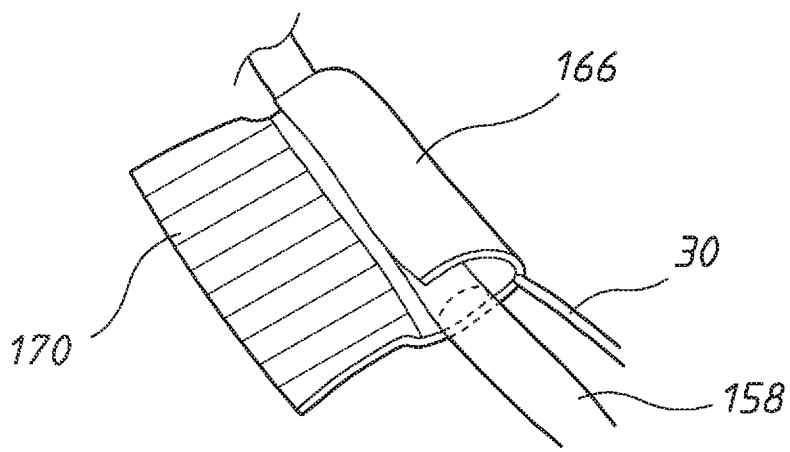
Figure 25C:
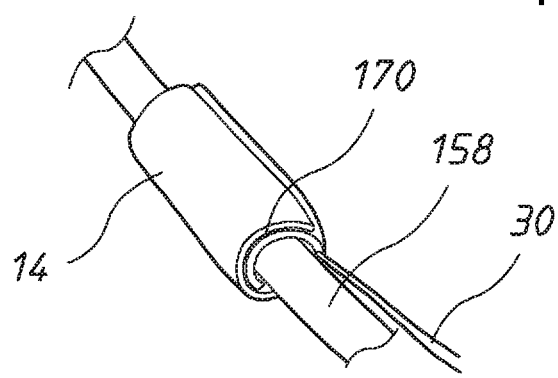
Figure 26:
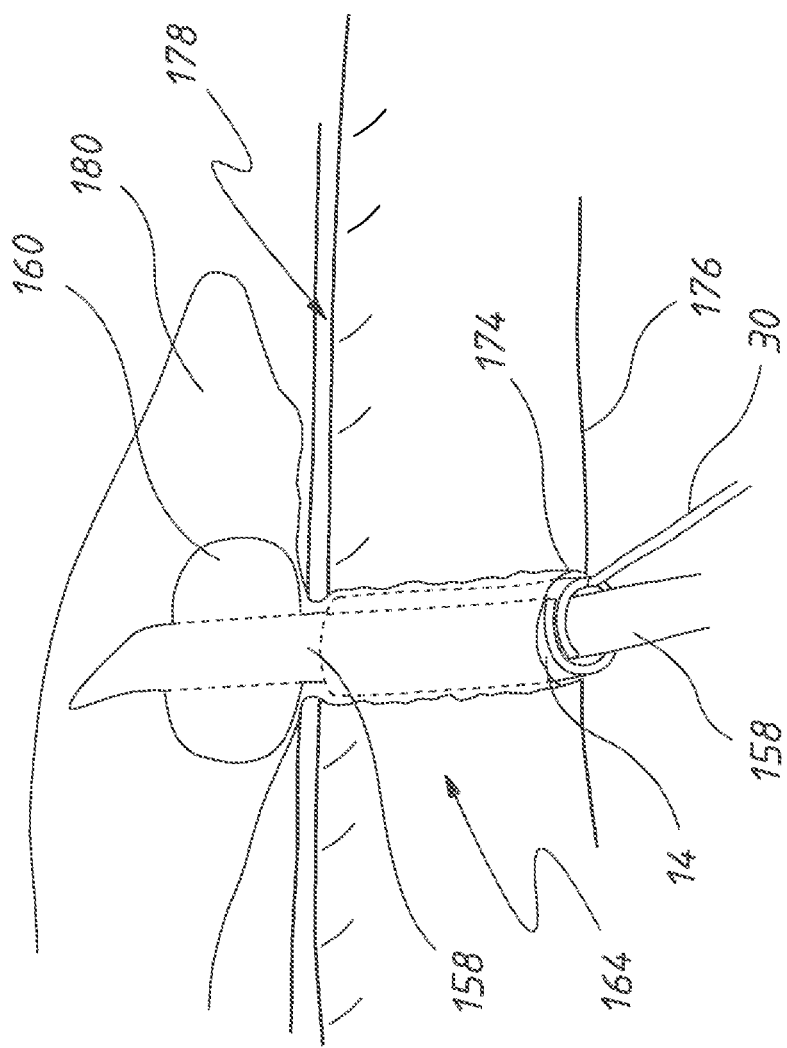

FIGS. 19A, 19B, 19C, and 19D illustrate the positioning of an endoVAC device embodied by the invention in a lumen of a patient utilising a guide wire and guide tube;

FIGS. 20A, 20B, and 20C illustrates the positioning of an endoVAC device embodied by the invention in the lumen of a patient utilising an endoscope;

FIGS. 21A, 21B, and 21C illustrate the positioning of an endoVAC device embodied by the invention in a lumen of a patient;

FIG. 22 is a diagrammatic view of another endoVAC device embodied by the invention in position in the rectum of a patient;

FIG. 23 illustrates a feeding tube inserted through a wound in the skin of a patient;

FIG. 24 is a diagrammatic side view of a device embodied by the invention;

FIGS. 25A, 25B, and 25C illustrate the wrapping of a porous element in the form of a sponge mat about a feeding tube; and FIG. 26 shows the device of FIG. 24 inserted through a wound in the skin of a patient.

DETAILED DESCRIPTION OF EXEMPLARY EMBODIMENTS OF THE INVENTION

Figure 1:
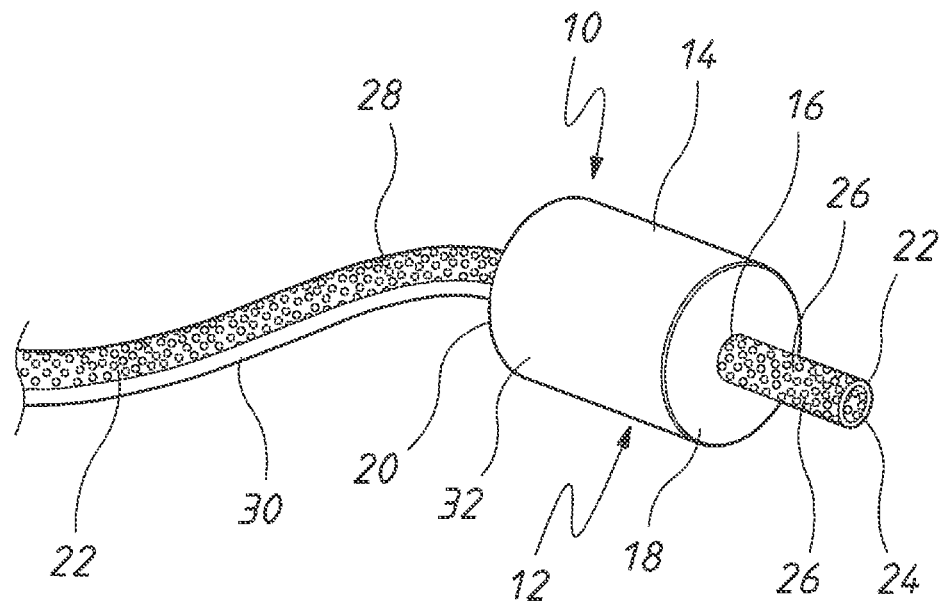
FIG. 1 is a diagrammatic perspective view of an endoluminal vacuum assisted closure (endoVAC) device.

The endoluminal vacuum assisted closure device (endo-VAC) shown in FIG. 1 comprises a porous element in the form of a substantially cylindrical biocompatible sponge 14 with a peripheral outer face for contact with an endoluminal surface of a patient and having a central through passageway indicated by the numeral 16 that extends from a proximal end 18 of the sponge to its opposite distal end 20. A drainage tube 22 fabricated from a physiologically acceptable plastic material is received in the through passageway of the sponge. The drainage tube allows for passage of bodily substances through the sponge and drainage from the lumen of the patient in use as further described below.

As can be seen, the drainage tube protrudes from the proximal end of the sponge 14 and terminates in an open end 24 for entry of the bodily substances into the tube. Further openings 26 for entry of the bodily substances into the interior of the drainage tube are provided in the side wall of the tube forward of the sponge. As also indicated in FIG. 1, the drainage tube 22 extends from the distal end 20 of the sponge, and is of a length sufficient to extend from the patient's body. Additional openings 28 are provided in the side wall of the tube for entry of bodily substances into the interior of the tube rearwardly of the sponge. That portion of the drainage tube 22 within the sponge is unperforated thereby sealing the interior of the drainage tube from the surrounding sponge. The sponge is fixed to the drainage tube along its length so as to retain the sponge in position whilst the device 10 is being inserted into position within the lumen. The sponge may be fixed to the tube by, for example, by the use of a suitable adhesive, or sonic or heat welding.

A suction tube 30 for connection to a suction source arranged externally of the patient's body is in fluid communication with the sponge 14 for application of a negative pressure to the sponge. Both the proximal and distal ends 18 and 20 of the sponge are essentially impermeable to gases and fluids, and so are adapted against egress of the bodily substances into the sponge under action of the suction applied to the sponge via the suction tube.

To seal the proximal and distal ends of the sponge against entry of the bodily substances, an occlusive barrier in the form of a ring of flexible plastic sheet material can be affixed to the respective ends in any suitable manner such as by an appropriate adhesive, heat or sonic welding, or other method. In this embodiment, the suction tube is sealingly received in, or terminates about, an opening provided in the ring of plastic sheeting affixed to the distal end of the sponge whereby the interior of the suction tube is in fluid communication with the sponge. Alternatively, the sponge can be provided with a flexible annular end cap formed from a suitable plastics material (e.g., a closed cell foam) that sealingly receives the suction tube and is affixed to the distal end of the sponge for application of the suction to the sponge via the suction tube. In such embodiments, the suction tube can open into a circumferential open channel defined in the underside of the annular cap wherein the open channel faces the distal end of the sponge for more even circumferential distribution of the applied suction to the sponge. Preferably, however, in other forms, the suction tube 30 extends into the sponge itself and has through openings in the side wall of that portion of the suction tube within the sponge. In further embodiments, an essentially impermeable coating can be applied to the respective end(s) of the sponge to seal the proximal and/or distal end(s) of the sponge rather than employing sheet plastics material or end/caps for this purpose, although any suitable method or means can be utilised.

By providing an occlusive barrier to the proximal and/or distal ends of the sponge 14 against the egress of gases, faecal matter and/or bodily fluids into the sponge 14 as described above, bacterial loading and "clogging" of the sponge 14 may be minimised.

The interior of the drainage tube is separated from the sponge along the entire length of the tube within the through passageway by the side wall of the tube. That is, there are no through openings in the side wall of the drainage tube between the proximal and distal ends of the sponge 14 ensuring the suction is applied to the peripheral face of the sponge.

Figure 2:
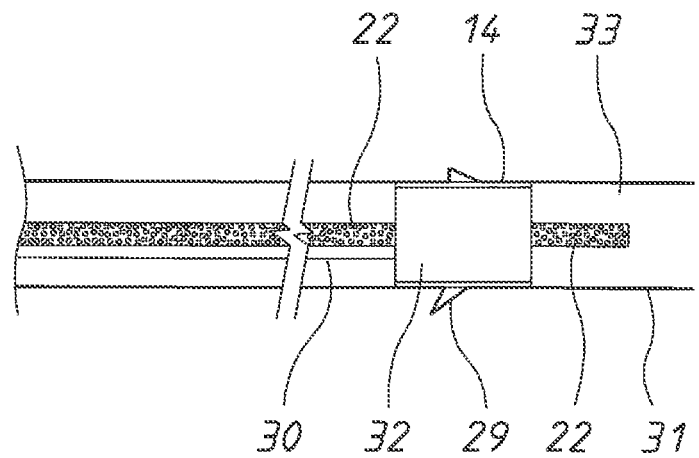
FIG. 2 is a diagrammatic partial side sectional view of the device of FIG. 1 in position within a lumen in the body of a patient.

With reference to FIG. 2, the peripheral outer face 32 of the sponge is in fluid communication with the suction tube through pores in the sponge, and is pressed against the wound 29 in the surrounding endoluminal surface 31 defining the lumen 33 in which the device 10 is placed in use. When in position, suction from the external suction source is thereby applied to wound and surrounding endoluminal surface via the outer face of the sponge 14. This creates a localised area of negative pressure about the wound, the suction drawing surface fluid and any exudate that may be present away from the wound into the sponge.

Thus, besides providing suction to the sponge, the suction tube 30 acts as a second drainage tube for fluids drawn through the sponge from the wound. Moreover, by diverting bodily substances present in the lumen through the sponge via the through passageway 16 and thereby separating those substances from fluids drawn into the sponge from the wound, clogging and/or fouling of the sponge by the bodily substance(s) in the lumen and associated loss of suction applied to the wound via the suction tube may also be reduced or avoided.

EndoVAC devices similar to that shown in FIG. 1 but which have an expandable element 34 disposed in the through passageway 16 of the sponge and more particularly between the drainage tube 22 and the sponge 14 are also expressly provided, wherein the expandable element is arranged to expand the sponge to press the peripheral outer face 32 of the sponge into firm with contact with the endoluminal surface.

Figure 3:
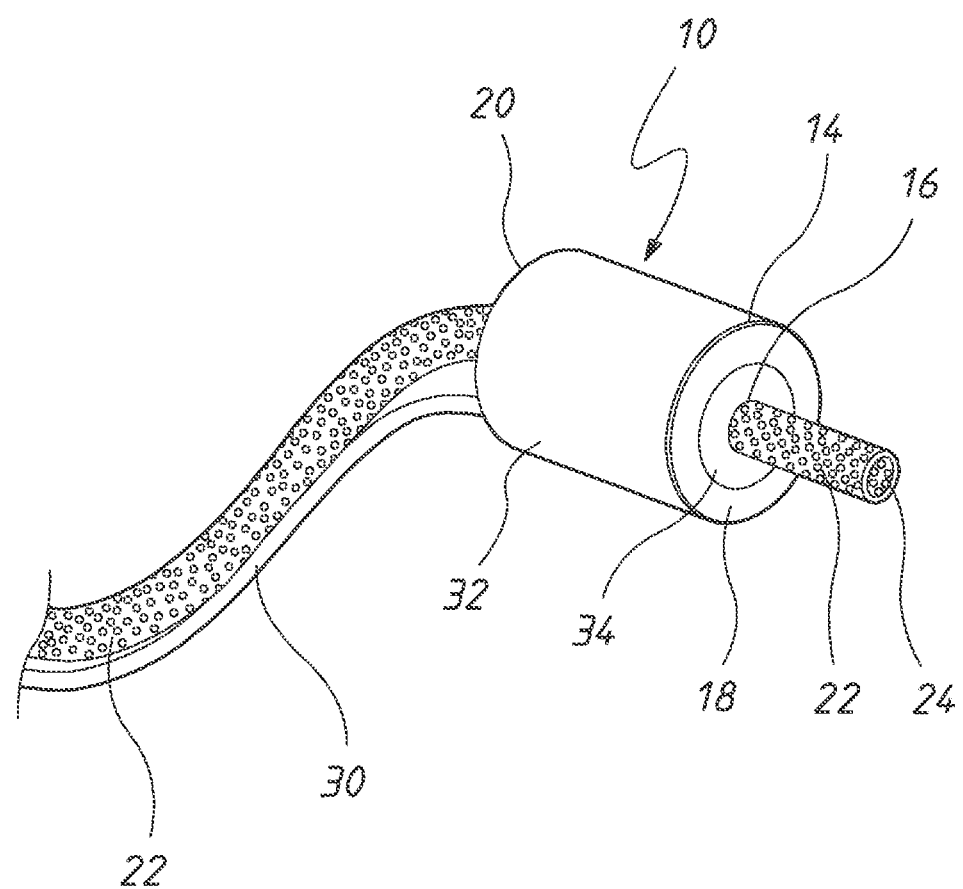
FIG. 3 is a diagrammatic perspective view of another endoVAC device.

The expandable element and can take various forms. For instance, in the embodiment illustrated in FIG. 3, the expandable element 34 is in the form of a tubular insert fabricated from a resilient material (e.g., a foamed plastics material) that is maintained in a compressed state about the drainage tube by a hollow locating tube/sheath (not shown) in which the surrounding sponge 14 is received whilst the device 10 is being located in position with the lumen adjacent the wound to be treated. The resilient material is biased to a normally expanded resting condition, and expands to that condition to press the sponge against the wound and surrounding endoluminal surface upon the insertion tube or sheath being withdrawn from the sponge once the device has been positioned within the lumen.

In another form, a further suction tube can be provided for applying suction/negative pressure to the resilient insert to compress the insert without the need to use a locating tube. In this embodiment, the peripheral surface of the resilient insert facing the sponge is sealed from the sponge (e.g., by an impermeable coating). As with the sponge 14, the proximal and distal ends of the insert are also sealed either by, for example, an impermeable coating or barrier as described in relation to FIG. 1. As such, withdrawal of the negative pressure applied to the resilient insert via the further suction tube allows the insert to expand to its normal resting condition and press the peripheral outer face of the sponge against the endoluminal surface.

Figure 4:
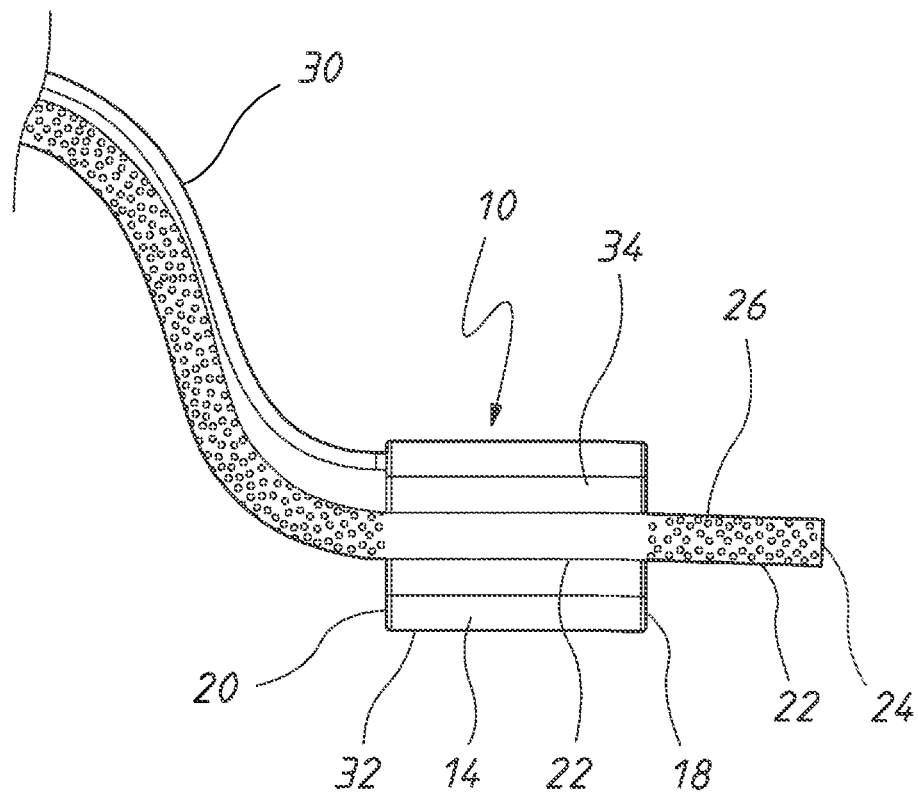
FIG. 4 is a diagrammatic side sectional view of another endoVAC device.

As a still further alternative, the expandable element 34 can take the form of an inflatable insert such as a tubular balloon with an inflation tube for inflation of the balloon to expand the peripheral outer face of the sponge into pressed contact with the endoluminal surface as generally illustrated in FIG. 4 (the inflation tube is not shown). The inflation tube can be connected to a hand operated pump externally of the patient's body for effecting inflation of the balloon to a predetermined pressure. To avoid over inflation, the pump is provided with a pressure safety valve and/or in other forms, a pressure gauge for indicating the pressure applied to the balloon. Once suitably inflated, a valve of the pump is closed to retain the balloon in the inflated condition.

From the above it will be understood that the term "expandable element" as used herein encompasses elements that can expanded from a compressed, collapsed or deflated condition in use to press the peripheral outer surface of the sponge 14 against the endoluminal surface. As such, the expandable element may normally exist in an expanded condition. Further, it will be appreciated that collapsing or compressing the sponge (with or without the use of a locating tube or sheath as described above) may assist passage of the device along the relevant bodily lumen into position by minimising frictional contact with the endoluminal surface.

Figure 5:
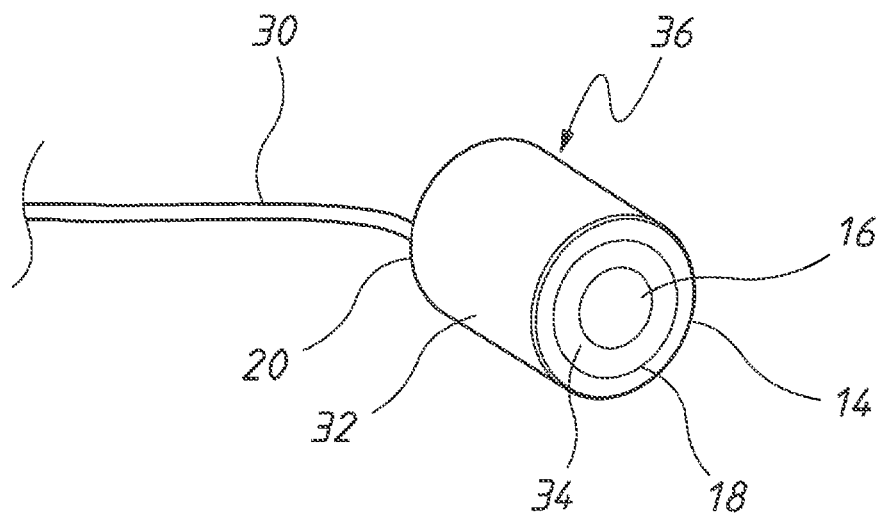
FIG. 5 is a diagrammatic perspective view of another endoVAC device.

Whilst the provision of a drainage tube 22 is desirable, it is not essential and embodiments of endoVAC devices as described herein can be provided without one as illustrated in FIG. 5. In this embodiment, bodily substances present within the lumen may simply pass through the through passageway 16 of the device 36 once the device is located in position.

When provided, the drainage tube can be connected to a programmable or other electric suction pump for drawing the relevant bodily substances through the device 10, 36 to assist drainage and sanitary collection of the substances from the patient for monitoring and/or subsequent disposal. The external suction source connected to the suction tube 30 may be the same or another electric pump, although any suitable source of suction can be utilised for providing suction/negative pressure to the drainage and suction tubes 22, 30 as required. In embodiments of an endoVAC device that is provided with a suction compressible resilient insert 34 as described above, that insert may be connected to the same or different suction source as the sponge 14.

EndoVAC devices described herein have particular application in the treatment of anastomotic wounds following surgery of the large bowel of the gastrointestinal (GI) tract for removal of cancerous tissue and to provide clear tissue margins in colorectal cancer (CRC) patients. Prior to the surgery (e.g., 24 hours beforehand), the patient's bowel is cleared of stool by the administration of laxatives such as dipropylene glycol and/or anemas. For cancer of the cecum or ascending colon, for example, a right hemicolectomy may be performed, whilst an extended hemicolectomy may be performed for cancer of the transverse colon. In patients with cancer of the descending or sigmoid colon, the surgery typically involves a left hemicolectomy or sigmoidectomy. In each of these surgeries, an anastomotic wound is formed by joining resected tissues and may be treated in accordance with the invention.

Figure 6:
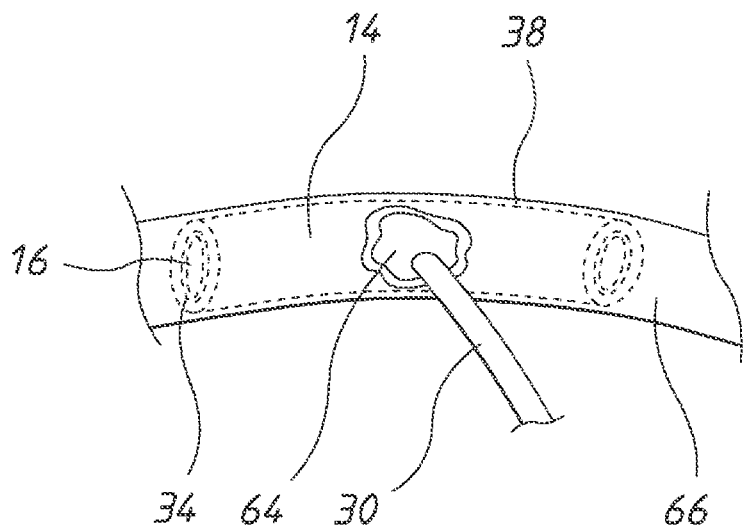
FIG. 6 is a diagrammatic view of another endoVAC device in position within a lumen in the body of a patient.

An endoVAC device as described herein may also be used to assist the healing of a fistula between e.g., the bowel and skin as generally illustrated in FIG. 6. In this embodiment, the device 38 is of the type having an expandable element 34 to press the surrounding sponge 14 into contact with the endoluminal surface of the bowel lumen 66 into which the fistula 64 opens. However, rather than the suction tube 30 applying suction to the distal end of the sponge or otherwise entering the distal end of the sponge, in this instance, the suction tube enters the device 38 through the side of the sponge and protrudes from the subject's body through the fistula. The suction tube can, for example, fork within the sponge such that one fork of the suction tube extends distally along within the sponge from the middle of the sponge and the other fork extends along within the sponge in the opposite direction to distribute the applied suction along the length of the sponge. The endoVAC device 38 can be inserted into position in the bowel through the fistula, and suction applied to the endoluminal surface around the fistula to promote healing. As healing of the fistula progresses and the tissue forming the opening of the fistula into the bowel is remodelled, the device 38 can be replaced with another device 38 of a smaller size by removing the previous device through the fistula and reinserting the smaller device in the same manner. Depending on the size of the fistula, this may be repeated on or more times.

Figure 7:
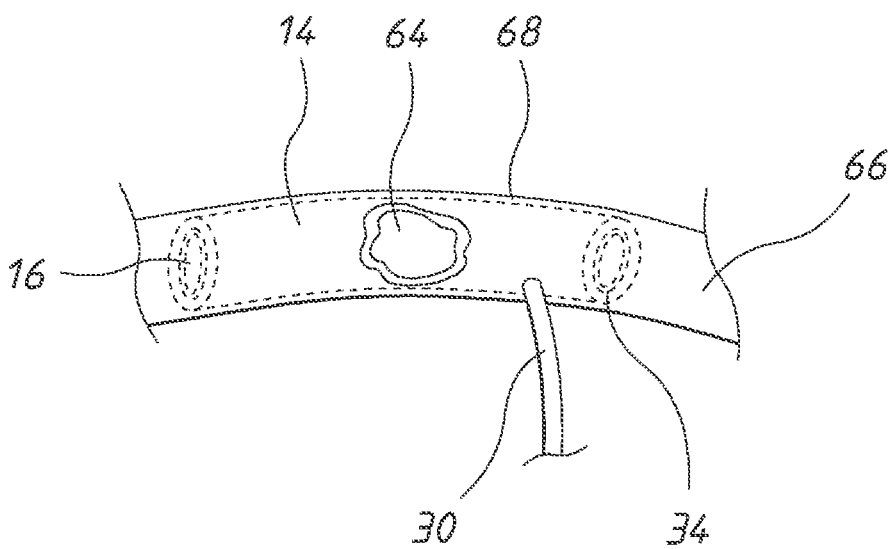
FIG. 7 is a diagrammatic view of another endoVAC device in position within the lumen in a body of a patient.

In another embodiment, an endoVAC device 68 can be located in position within the bowel so as to cover the opening of a fistula 64 but wherein the suction tube 30 enters the bowel through a surgically made opening along from the fistula as illustrated in FIG. 7.

Figure 8:
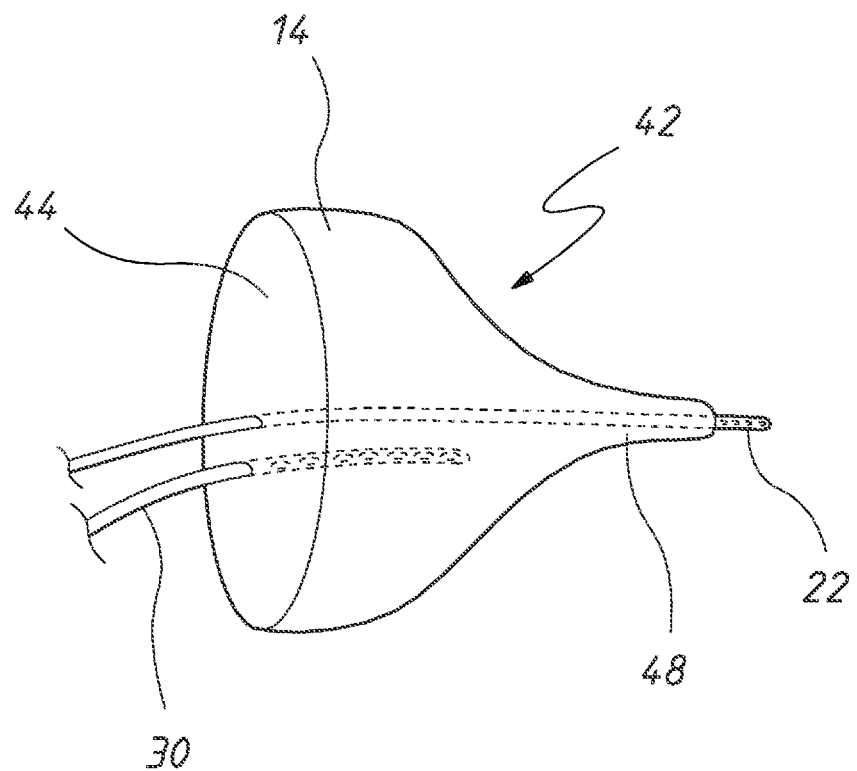
FIG. 8 is a diagrammatic view of another endoVAC device.

An endoVAC device 42 suitable, for example, use in healing in a pancreatojejunostomy in which the resected pancreas is surgically sutured to the middle region of the small intestine between the duodenum and ileum known as the jejunum is shown in FIG. 8. In this device the sponge 14 is funnel shaped wherein the drainage tube 22 and the suction tube 30 enter the distal face 44 of the sponge, the distal face 44 of the sponge being otherwise sealed against egress of gas and fluid into the sponge as described above. As shown, that portion of the suction tube 30 within the sponge is provided with a number of through openings along its side wall, and the outer diameter of the sponge generally decreases in the distal to proximal direction of the sponge forming a projection of the sponge in the form of a shaft 48 from which the drainage tube 22 extends. The shaft 48 of the sponge can be inserted into a resected end of the pancreatic duct in a pancreatojejunostomy or in the resected end of a duct in other surgical procedure(s) to assist the healing process. The pancreatic duct carries pancreatic juice from the pancreas to the small intestine. Pancreatic juice is alkaline and contains enzymes which act to break down fat, and so can cause significant damage outside of the intestine. The "leakage rate" for pancreatojejunostomies is in the order of about 15%.

Figure 9:
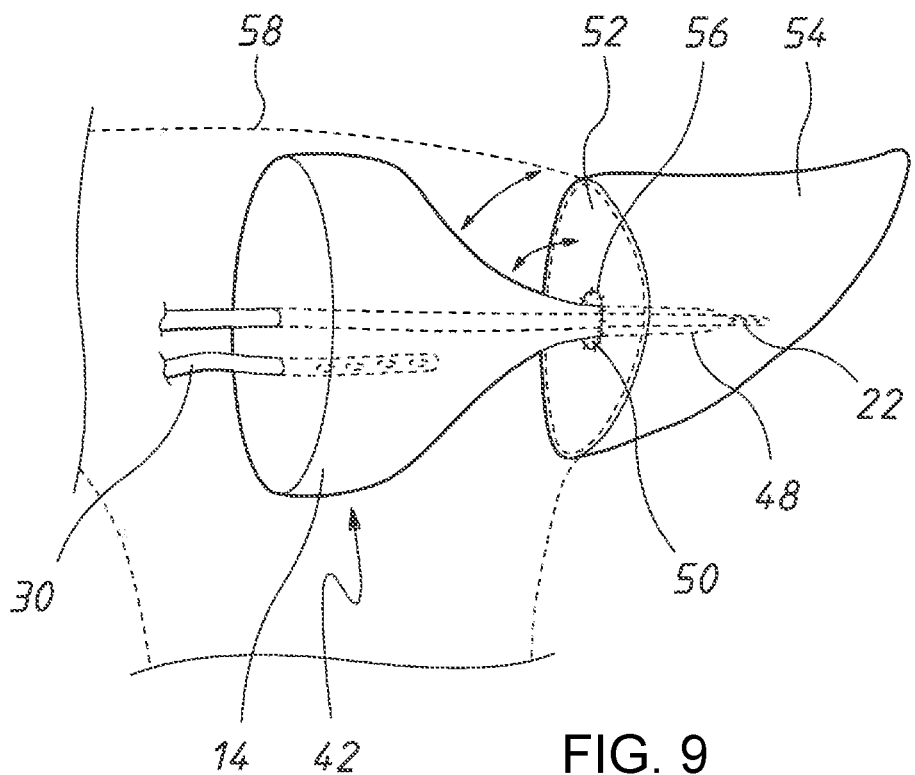
FIG. 9 illustrates the device of FIG. 8 inserted in the pancreatic duct of a pancreas sutured to the jejunum of the small intestine in a pancreatojejunostomy.

An example of a pancreatojejunostomy technique in which the exposed opening of the pancreatic duct 50 in a resected end 52 of the pancreas generally indicated by the numeral 54 is sutured to the mucosa of the jejunum by sutures 56 such that the duct opens into the jejunum 58 through an opening surgically formed in the jejunum is illustrated in FIG. 9. In the embodiment shown, the endoVAC device 42 is located within the lumen of the jejunum and the projecting shaft 48 of the sponge 14 is inserted into the open end of the pancreatic duct 50. The suction applied to the sponge via the suction tube 30 may assist to not only facilitate healing of the resected end of the pancreatic duct but also the suturing injury to the mucosa of the jejunum. The side wall of the jejunum adjacent to the pancreatic duct would also be expected to approximate to the funnel shape of the sponge, the suction applied to the sponge by the suction tube assisting to retain the side wall of the jejunum against the sponge and the shaft 48 of the sponge in position within the pancreatic duct. That is, the outer peripheral face of the sponge and at least the endoluminal surface of the jejunum about the sponge would change shape under the effect of the applied suction to conform to each other as indicated by the double headed arrows.

In some embodiments, at least that portion of the drainage tube 22 within the sponge extending longitudinally through the shaft can comprise an expandable stent sealed from the surrounding through passageway of the sponge by an expandable sleeve or layer of a suitable plastics material. Alternatively, for instance, the through passageway of the sponge in which the stent is received may be sealed from the stent in some other manner. As shown in FIG. 8 and FIG. 9, the shaft 48 of the sponge tapers in the distal to proximal direction. However, in other embodiments, the diameter of the sponge's shaft 48 may be essentially constant. Further, the proximal end of the shaft 48 may be sealed against egress of bodily fluids into the sponge although this is not essential in all embodiments of this type as the exposed proximal end of the shaft 48 when in position in the pancreatic or other duct and pressed against the surrounding endoluminal surface of the duct will typically be of minimal thickness.

Figure 10:
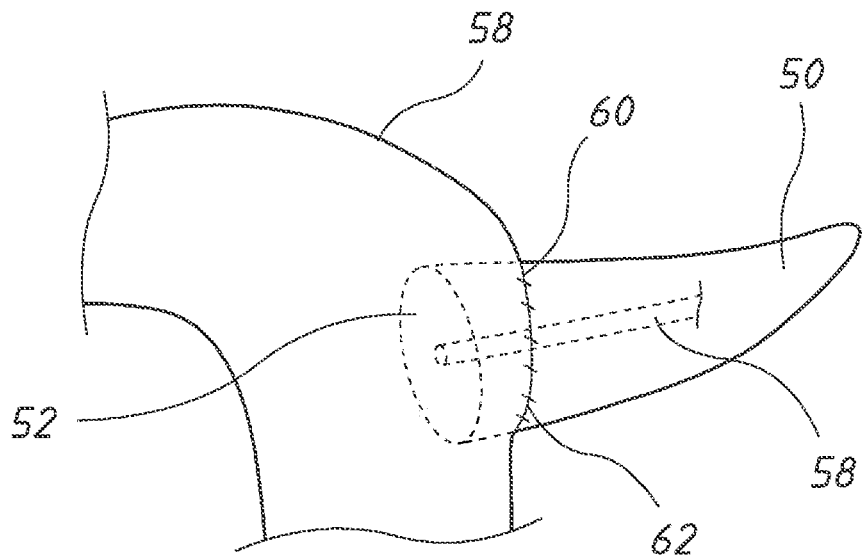
FIG. 10 illustrates a pancreas sutured to the jejunum of the small intestine in a pancreatojejunostomy employing the "dunk technique"

A further pancreatojejunostomy technique in which the entire resected end portion of the pancreas is inserted into an opening 60 formed the side wall of the jejunum 58 whereby the opening in the side wall is sutured to the pancreas by sutures 62 is illustrated in FIG. 10. The shaft 48 of the endoVAC device 42 is again inserted into the resected opening of the pancreatic duct 58 to assist healing of the duct and resected face 52 of the pancreas, as well as the suturing injury to the pancreas and jejunum. As in the embodiment illustrated in FIG. 9, contact of the funnel shaped main body of the sponge 14 with the endoluminal surface of the jejunum and the resected face of the pancreas 54 under the action of the suction applied to the sponge via the suction tube 30 further assists to retain the sponge in position.

In at least some embodiments, an endoVAC device as described herein may be provided with another respective porous element disposed proximal to (forward) and/or distal to (rearwardly of) the sponge 14 for collection of bodily substances within the relevant lumen 33 and drainage away from the sponge 14 via the drainage tube 22, thereby reducing the risk of the sponge 14 becoming occluded or blocked. The provision of additional such porous element(s) is particularly suitable in embodiments shown in FIG. 1 to FIG. 7, although the provision embodiments of an endoVAC device as shown in FIG. 8 with an additional porous element disposed forwardly and/or rearwardly of the sponge 24 of that device wherein the additional porous element is sealed or separated from the sponge by a respective occlusive barrier such as a fluid impermeable barrier or other means as described above is also expressly encompassed.

Figure 11:
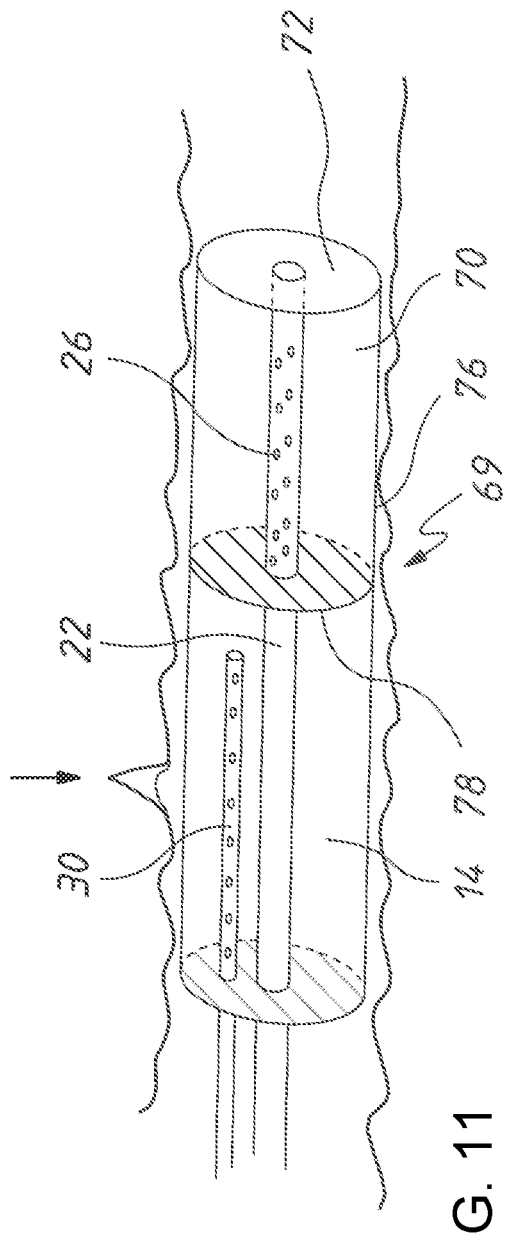
FIG. 11 is a diagrammatic view of an endoVAC device embodied by the present invention.

FIG. 11 shows an embodiment of an endoVac device 74 of the invention provided with another absorbent element besides the sponge 14. As shown, the further absorbent element is also in the form of a sponge 70 that is located forwardly of sponge 14 to which suction is applied (i.e, the "VAC sponge") via the suction tube 30. The drainage tube 22 passes through the "proximal" sponge 70 and opens to the end face 72 of that sponge. Whilst the proximal sponge 70 is absorbent and so facilitates the absorption of bodily liquids and substances into its end face 72 and outer peripheral side surface 76 for passage into the drainage tube 22, the proximal sponge is joined to the sealed end of the VAC sponge 14 forming a juncture indicated by the numeral 78. The juncture/sealed proximal end face 78 of the VAC sponge blocks bodily substances that enter the proximal sponge 70 from passing into the VAC sponge 14, for entry of those substances into the drainage tube 22 and drainage away from the VAC sponge via the drainage tube. The proximal sponge may thereby, reduce the risk or incidence of bodily substances "leaking" around the sealed proximal end 78 of the VAC sponge and so, the potential for fouling or blockage of the VAC sponge 14.

Figure 12:
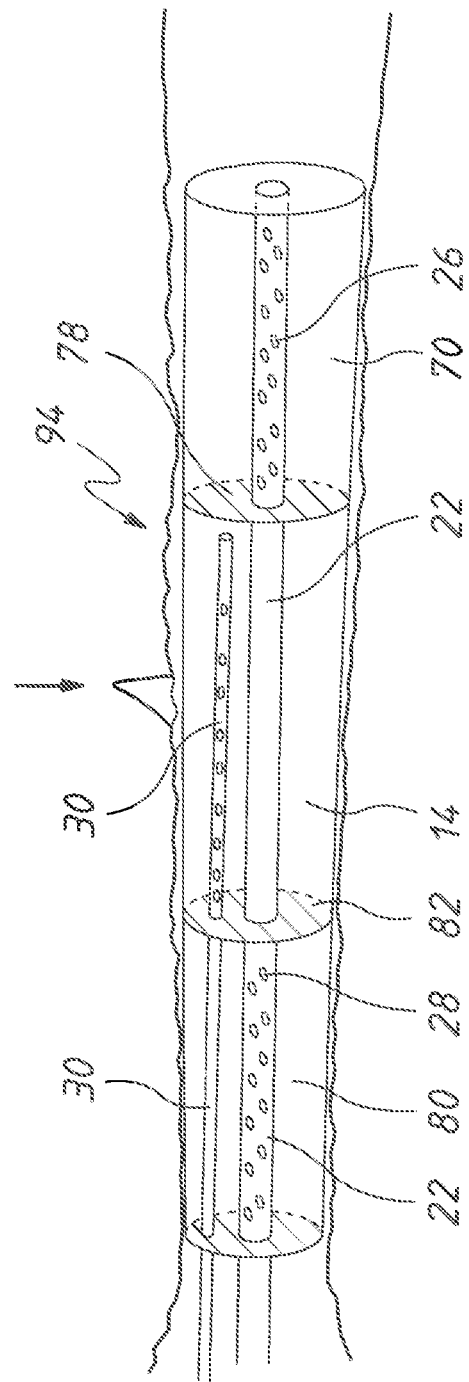
FIG. 12 is a diagrammatic view of another endoVAC device embodied by the invention.

An endoVAC device 94 embodied by the invention provided with a respective porous element in the form of an absorbent sponge disposed forward and rearwardly of the VAC sponge 14 is shown in FIG. 12. In this embodiment, the drainage tube 22 passes through both the proximal sponge 70 and the "distal" sponge 80 for entry of bodily fluids and other bodily substances into the drainage tube via openings 26 and 28. As can be seen, the front end of the distal sponge is joined to the sealed distal end of the VAC sponge 14 forming a juncture indicated by the numeral 82 against the passage of bodily substances from the distal sponge into the VAC sponge 14. Similarly to the embodiment shown in FIG. 11, the interior of the drainage tube 22 does not open into the VAC sponge, and the suction tube 30 does not open into either of the proximal or distal sponges 70 and 80. The unnumbered arrows in FIG. 11 and FIG. 12 indicate the wound. The juncture(s) (e.g., 82) between the sponge 14 and the proximal sponge 70 and/or the distal sponge 80 may be formed by an occlusive adhesive joining the sponge 14 and proximal 70 and/or distal sponge 80 together. Alternatively, respective of the juncture(s) may, for example, be provided by a sheet of suitable plastics material to which the respective ends of the sponges are affixed and which provides an impermeable barrier to the bodily substances although, any other appropriate method may be utilised.

In accordance with another embodiment of the invention, an endoVAC device as described herein such as shown in any one of FIG. 1 to FIG. 12 can be provided in which the suction tube 30 receives the drainage tube 22 so as to be essentially concentric therewith as illustrated in FIG. 13. As shown in FIG. 13, the leading end of the suction tube 30 sealingly terminates about the drainage tube 22 at the proximal end of the VAC sponge 14, and the outer circumference of the drainage tube 22 is generally spaced from the interior circumference of the suction tube 30 defining an interior lumen 84 of the suction tube about the drainage tube. Whilst not shown, the distal end region of the drainage tube may sealingly passes through the suction tube to an external port for connection of the drainage tube tube to a collection receptacle and/or suction pump as described above. Likewise, the distal end of the suction tube 30 can open to an external port adapted for connection to the same or a different suction source. Providing the drainage tube 22 within the suction tube 30 allows optimum positioning of the suction tube along the longitudinal axis of the endoVAC device for application of suction to the VAC sponge 14, and maximisation of the outer diameter of the suction tube for application of suction to the VAC sponge.

As also shown in FIG. 13, an endoVAC device as described herein can include one or more irrigation channels arranged for irrigation of at least one of the drainage tube 22, the suction tube 30, and the VAC sponge 12 with a physiologically acceptable irrigation fluid. More particularly, in the embodiment shown, an irrigation conduit 85 forming a first irrigation channel lies alongside drainage tube whilst a further irrigation conduit 86 defining a second irrigation channel lies alongside the suction tube 30. In use, the conduits 85 and 86 are connected to a source of the irrigation fluid which flows from the respective open ends 88 and 90 of the conduits into the drainage tube and suction tube to irrigate them whereby the risk of blockage of the drainage tube and suction tube may be reduced.

Another embodiment of an endoVAC device embodied by the invention is shown in FIG. 14. In this embodiment, a further irrigation conduit 92 is provided defining an irrigation channel for irrigation of the VAC sponge 14 as well as irrigation conduits 85 and 86 for irrigation of the drainage and suction tubes 22 and 30. As can be seen, the irrigation conduit 92 is has a closed proximal end 94 but is provided with a plurality of spaced apart outlet ports 95 substantially along the length of the VAC sponge 12 that are orientated toward the outer circumferential face of the VAC sponge for feeding the irrigation fluid into the sponge. Whilst the "vacuum" and "drainage" tube irrigation conduits 86 and 85 shown in FIG. 13 and FIG. 14 are only provided with a singlet out for the irrigation fluid, embodiments can also be provided in which one or both of these conduits may also provided with a plurality of spaced apart outlet ports therealong for the irrigation fluid.

The irrigation fluid can be any suitable fluid conventionally used for the irrigation of wounds and/or bodily tissues, such as a sterile water or a physiological saline preparation, and is typically drip fed into the drainage tube, suction tube and/or the VAC sponge 14 as applicable under the action of gravity or applied pressure (e.g., via use of a peristaltic or other pump(s)). While the respective irrigation conduits (i.e., 85, 86 and 92) can be fed from the same source of physiologically acceptable fluid, embodiments of endoVAC devices in accordance with the invention may be provided in which different such irrigation fluids can be fed into different one(s) of the irrigation conduits.

Figure 15:
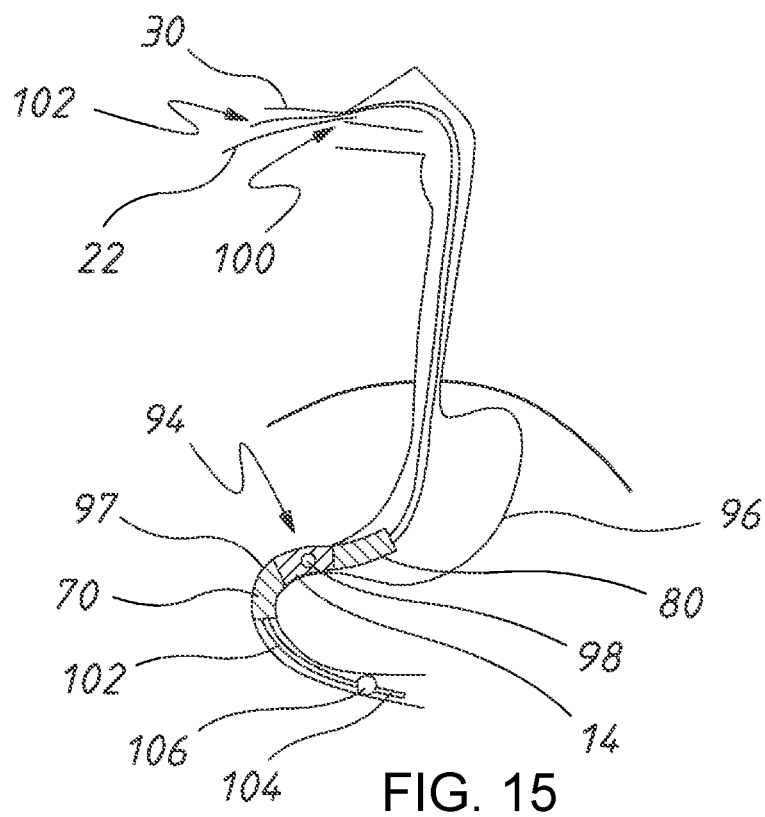
FIG. 15 illustrates an endoVAC device embodied by the invention in position in the duodenum of a patient.

In yet another aspect of the invention, a flexible feeding tube can be inserted down the through passageway 16 of an endoVAC device described herein (and hence the drainage tube 30 when present), such as when the device is used in the upper respiratory tract, G.I tract or more generally the digestive tract of a patient to facilitate feeding and/or hydration of the patient whilst the device is in position. An example utilising an endoVAC device of the type of FIG. 12 is shown in FIG. 15 wherein the device 94 is situated in the duodenum 97 below the stomach 96 for assisting the healing of a duodenal ulcer indicated by the numeral 98. As generally illustrated, the drainage tube 22 and suction tube 30 pass from the nasal passage 100 of the subject, and the feeding tube 102 extends down the drainage tube through the distal and VAC sponges 80 and 14, and protrudes from the drainage tube and proximal sponge 70 for post-pyloric feeding of the subject. The feeding tube 102 utilised in this embodiment is a Foley catheter type tube provided with a weighted open proximal tip 104 to assist insertion of the feeding tube down the drainage tube 22, and an inflatable balloon 106 (shown in an inflated condition) disposed rearwardly of the weighted tip. The feeding tube is provided with two internal longitudinal lumens. More specifically, an "inflation" lumen opens into the balloon 106 for inflation or deflation of the balloon, and is connected at its distal end to a valve for being closed to maintain the balloon in an inflated condition or subsequently opened when the balloon is to be deflated. The other "feeding" lumen is a through passageway that opens from the weighted tip 104 of the feeding tube in the lumen of the gastrointestinal tract for passage of nutrient and/or fluid preparations into the G.I tract. The lumens of the feeding tube 102 are divided from one another and open into respective external ports provided at the opposite distal end region of the feeding tube.

Nutrients and/or fluid preparations can be loaded into a syringe fitted to the external port for the "feeding lumen" and fed into the G.I tract of the patient under the action of gravity, or by operation of a plunger fitted in the barrel of the syringe. The balloon 106 when inflated presses against the surrounding endoluminal wall defining the lumen of the G.I tract in which it is placed. This assists not only to retain the proximal/leading end of the feeding tube 102 in position, but also blocks or inhibits undesirable back flow of administered nutrient and/or fluid preparations toward the proximal sponge 70 of the endoVAC device. The balloon 106 can be inflated in the manner conventionally used for inflation of balloon catheters such as by a hand operated "squeeze" pump fitted to the external port of the inflation lumen. Generally, a pressure gauge arranged for monitoring the inflation status of the balloon and/or over pressure safety release valve for ensuring the balloon is not over inflated is/are also provided.

Figure 16:
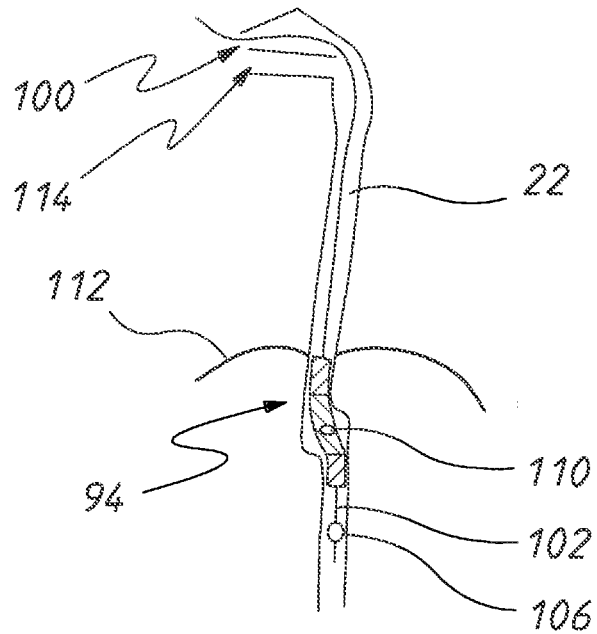
FIG. 16 illustrates an endoVAC device embodied by the invention in position in the gastric pouch of a patient.
Figure 17:
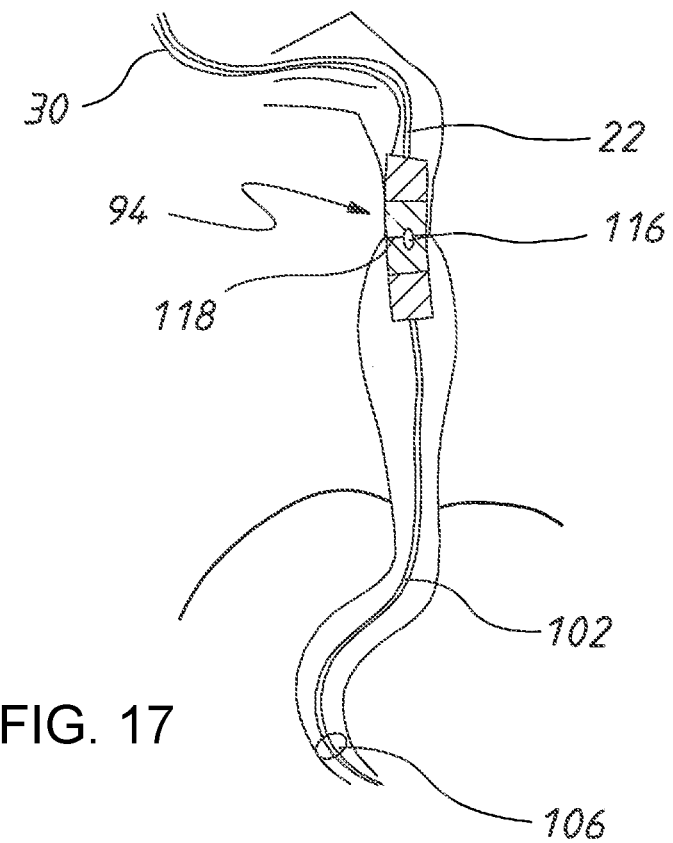
FIG. 17 illustrates an endoVAC device embodied by the invention in position in the upper gastrointestinal (G.I) tract of a patient.

Further embodiments of an endoVac device embodied by the invention of the general type illustrated in FIG. 12 are respectively shown in FIG. 16 and FIG. 17. In particular, FIG. 16 shows an endoVac device 94 situated in the gastric pouch indicated by the numeral 108 for treating a leakage or anastomosis 110 in the G.I tract following gastric bypass surgery. Again, a feeding tube 102 with a balloon 106 disposed on its proximal end region is inserted down the drainage tube 22 and extends beyond the proximal sponge for feeding and/or hydration of the patient as described above. The diaphragm of the patient is indicated by the numeral 112 whilst the nasal passage and mouth of the patient are respectively indicated by 100 and 114. FIG. 17 also shows a feeding tube with an inflatable balloon 106 in combination with an endoVac device in the manner described above. Although in this instance, the endoVac device 94 is situated in the upper G.I tract wherein the VAC sponge 14 is aligned with a leak 116 in an anastomosis 118 following an esophyectomy.

Figure 18:
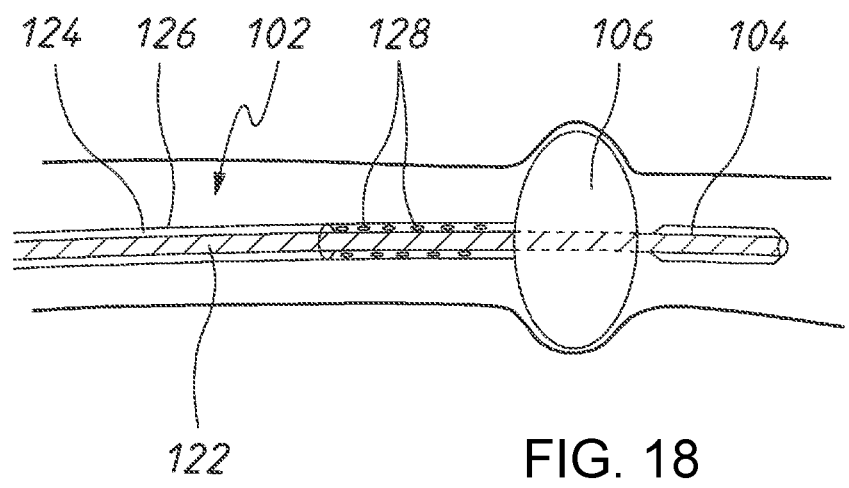
FIG. 18 illustrates a feeding tube with a balloon for being inflated in a lumen of a patient.

In at least some embodiments, a feeding tube 102 provided with an inflatable balloon 106 on its proximal end region can include a further longitudinal internal lumen for drainage of bodily fluids and other bodily substances that may pool or accumulate to the distal side of the balloon 106 when the balloon is inflated as diagrammatically illustrated in FIG. 18. In the embodiment shown, the "feeding" lumen is defined by an internal longitudinal conduit 122 about which the "drainage" lumen 124 is defined by the feeding tube's outer wall 126. To allow entry of bodily fluids and other bodily substances into the drainage lumen, a plurality of through openings 128 are provided in the outer wall 126 of the feeding tube rearwardly of the balloon 106. The distal end of the drainage lumen 124 may terminate in a further external port for connection to a suction source to assist drainage of bodily substances from the drainage lumen into a collection receptacle. The "inflation" lumen for inflation or deflation of the balloon is not shown. However, the inflation lumen may, for instance, be provided by a longitudinally extending conduit disposed within the drainage lumen.

Figures 19A, 19B, 19C, 19D:
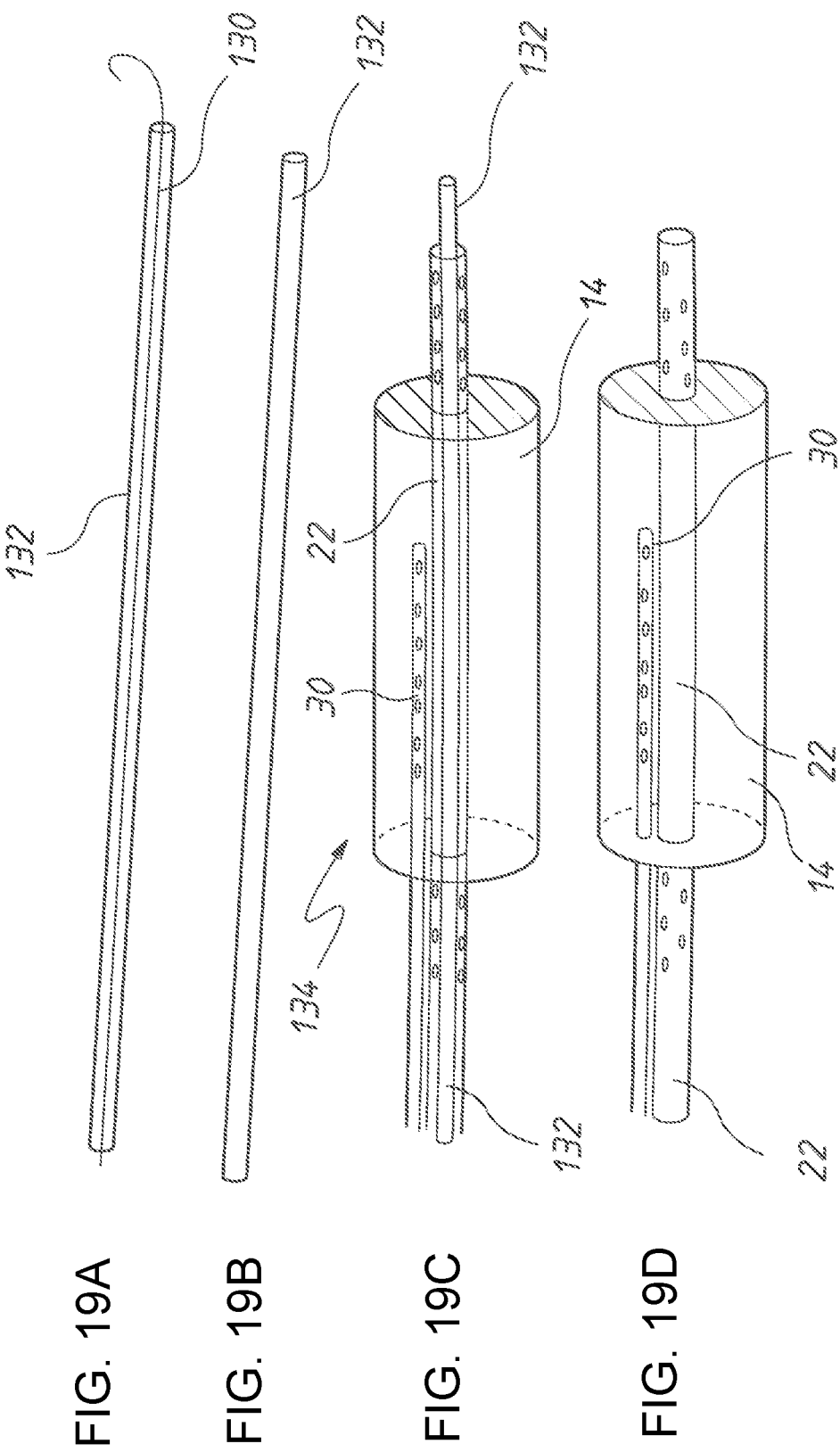

The placement of an endoVac device as described herein in position is illustrated in FIGS. 19A, 19B, 19C, and 19D. More particularly, as shown in FIG. 19A, a guide wire 130 is first inserted into the relevant bodily lumen of the patient, and an overwire stent/guide tube 132 is then slid down over the guide wire prior to the guide wire being withdrawn to leave the guide tube 132 in position within the lumen (see FIG. 19B-19C). The endoVAc device 134 is then in turn slid down the guide tube 132 as illustrated in FIG. 19D such that the guide tube is received by the drainage tube 22 of the endoVAC device (or more generally, through the through passageway 16 of the device), and the guide tube 132 is subsequently withdrawn whereby the endoVAC device 134 is left in position within the lumen of the patient.

An endoscope type viewing device (e.g., such as a rigid or semi-flexible sigmoidoscope or colonoscope) desirably having slight or suitable curvature as required may also be employed to locate the endoVAC device in position adjacent to the wound to be treated, such as, for example, in the large bowel of the anus. In this instance, the endoVAC device may be mounted on the end of the endoscope and/or otherwise be moved along the lumen of the large bowel as the endoscope is inserted into the patient as, for instance, illustrated in FIGS. 20A, 20B, and 20C. As shown, a push overtube 136 and the endoVAC device 138 can be preloaded on the endoscope whereby the endoscope is again inserted in the drainage tube 22 (and/or through passageway 16) of the endoVAC device. The endoscope is used to guide the endoVAC device 138 along the lumen whilst the endoVAC device is maintained in position on the endoscope by maintaining the overtube in abutment with the distal end of the VAC sponge 14 (or distal sponge 80 when provided). Once the endoVAC device 138 is in position, the endoscope is withdrawn from the patient whilst the overtube 136 is used to retain the endoVAC device in position. The overtube 136 is then withdrawn from the patient.

However, any essentially rigid elongate introducer may be used alone or with another instrument (e.g., a push overtube or stylette for being pressed against the VAC sponge 14 or distal sponge 80) to position the endoVAC device in the bodily lumen as described above. For example, the introducer can be in the form of an essentially rigid tube such as an internal circular surgical stapler with an angled proximal end suitably dimensioned for insertion into or through the drainage tube 22/through passageway 16 of the endoVAC device.

The VAC sponge 14 (and adjacent proximal and distal sponges 70 and 80 when provided) may be held in a collapsed or compressed condition to facilitate being moved into position along the bodily lumen of the patient as described above in relation to FIG. 3 and FIG. 4. Whilst this can be achieved with the use of a hollow locating tube or sheath, in another embodiment a covering (e.g., a heat-shrink wrap or other film of suitable plastics material) wrapping around the peripheral outer face (e.g., 32) of the sponge(s) (14, 70, 80) that holds the sponge in a collapsed or compressed condition may be provided, wherein the covering is peeled or drawn from the sponge(s) once the endoVAC device is in position thereby allowing the sponge(s) to expand (or be expanded) into pressed contact with the surrounding endoluminal surface. In one or more embodiments, the covering may have a frangible tear line for being torn to facilitate removal of the covering from the sponge(s) and/or an outer friction reducing coating (e.g., teflon or a physiologically acceptable lubricant) for reducing friction between the coating and endoluminal surface of the subject.

An example of this embodiment is generally illustrated in FIGS. 21A, 21B, and 21C which show an endoVAC device 140 in accordance with the invention loaded over an overwire stent or other suitable guide tube 132, wherein the guide tube is inserted through the drainage tube 22 of the device. The VAC sponge 14 of the device is held in a compressed condition for location within the bodily lumen of the subject by a covering in the form of a plastic wrap 142 that surrounds the outer peripheral face 32 of the VAC sponge and negative pressure applied to the VAC sponge 14 via suction tube 30 (and/or to e.g., an underlying expandable element 34 in the form of a resilient insert or the like as described above by a further suction tube), as illustrated in FIG. 21A. As the wrap 142 is drawn from the VAC sponge 14 the proximal end region of the sponge begins to expand into its normal expanded resting condition as shown in FIG. 21B. The VAC sponge resumes its full normally expanded condition when the wrap 142 is removed entirely as shown in FIG. 21C. The guide tube 132 may then also be withdrawn although in some embodiments, the guide tube 132 may be withdrawn prior to the removal of the plastic wrap 142.

To facilitate the removal of the covering 142 it may be provided in a length sufficient for it to protrude externally from the subject's body so that it can be manually gripped and pulled rearwardly to unsheath the sponge(s) (14, 70, 80 as applicable) whilst the endoVAC device is retained in position with a push overtube (e.g., 136), stylette or the like. Alternatively, the covering may be of sufficient length for direct attachment (e.g., by an adhesive tape of clamp) to an endoscope or other introducer used for locating the endoVAC device in position, so that the covering is drawn from the sponge(s) when the endoscope or other locator is withdrawn. As still another option, a dedicated rod, catheter or the like attached to the covering can be inserted in position with the endoVac device whereby the covering is peeled and/or drawn from the sponge(s) with withdrawal of the rod or the like. Rather than self-expanding into pressed contact with the surrounding endoluminal surface, the sponge(s) of an endoVAC device provided with an inflatable expandable element 34 (e.g., a balloon) can be expanded into pressed contact of with the endoluminal surface by inflation of the balloon 34 as also described above.

Another embodiment of an endoVAC device for treating a fistula, wound or leak indicated by the numeral 144 in the rectum of the subject with an inflatable expandable element in the form of an inflatable bladder 34 is illustrated in FIG. 22. In this embodiment, the drainage tube 22 is funnel shaped to assist collection of stool and faecal matter. When located in position, the bladder is inflated via an inflation tube (not shown) to expand the VAC sponge 14 into pressed contact with wound 144 in the endoluminal surface of the rectum. To assist maintaining the proximal terminal "funnel" rim 146 of the drainage tube 22 fully open, the rim may be formed by an inflatable annular compartment of the drainage tube. The inflatable compartment may be in fluid communication with the bladder 34 so as to be inflated simultaneously with the bladder, or be inflatable via a separate inflation line.

To assist positioning on an endoVAC device as described herein within an endoluminal space such as that of the upper or lower G.I tract, the location of the device may be monitored by ultrasound or, for example, a fluoroscopic technique employing a contrast agent, by another surgeon or medical attendant.

As a further alternative for vacuum assisted wound therapy, instead of using an endoVAC device within a lumen of the patient such that the device lies along the lumen and the sponge 14 is entirely internalised within the patient as described above, a sponge or other flexible porous element under negative pressure as described herein can be employed for vacuum assisted treatment of tissue around a central venous catheter line, permanent drain, feeding tube, or other such tube inserted through the skin of a patient.

Drains and other tubes entering the body through a wound (e.g., a fistula or a surgically created opening) in the skin of a patient provide a source of continued irritation to the wound. This can be exacerbated by the leakage of fluids from between the tube and surrounding wound, which can result in exoriation, erosion and in more serious instances, chronic ulceration about the tube entry site. This is particularly the case where a feeding tube or drain is inserted through the skin into the G.I tract, where G.I secretions/fluids (e.g., acid, enzymes, bile etc.) can leak through the skin wound site between the tube and wound as illustrated in FIG. 23, where a feeding tube 148 provided with a Foley type inflatable balloon 150 and passing through a wound 152 in the skin of a patient is shown. The flow of fluids/secretion between the inflated balloon 150 and the endoluminal mucosa, across fascia tissue and out between the feeding tube 148 and skin 152 is shown by arrows 154.

As such, in another aspect of the invention there is provided a device for applying a negative pressure to a wound in the skin of a patient, the device comprising, an insertion tube for insertion into the wound, a flexible porous element for being inserted into the wound for application of the negative pressure to the wound, and a suction tube for being connected to a suction source externally of the patient's body and which is in fluid communication with the porous element to apply the negative pressure to the porous element with operation of the suction source, wherein the porous element is mounted to the insertion tube.

As in embodiments described above, the porous element can comprise an absorbent sponge. Typically, of the opposite proximal and distal ends of the sponge at least one of them is adapted (e.g., sealed) against the egress of bodily substances into the sponge and most typically, at least the proximal end.

Typically, the insertion tube passes through the sponge. In at least some embodiments, the insertion tube is received in a through passageway of the sponge as generally described above. However, in at least some embodiments, the sponge may be in the form of a mat which in use, is wrapped around the insertion tube.

Typically, the device further includes a fastening system for fastening the mat when wrapped around the tube to retain the mat in a wrapped condition. The fastening system may comprise a "hook tape" (e.g., of the Velcro™ type) system although any suitable fastening system can be utilised.

The insertion tube of the device according to this aspect of the invention may also comprise an inflatable balloon disposed proximally forwardly of the sponge, the balloon being inflatable to anchor the insertion tube in position within the lumen of the patient.

An embodiment of this aspect of the invention is diagrammatically shown in FIG. 24. The vacuum sponge device 156 shown comprises an insertion tube in the form of standard type feeding tube 158 with a Foley balloon 160 (shown in an inflated condition here) as generally described above in relation to FIG. 16. A VAC sponge 14 is provided in position on the feeding tube 158 rearwardly of the balloon for insertion into the wound entry in the skin such that the peripheral side face 159 of the VAC sponge 14 is pressed against the surrounding wound. The sponge 14 has a central through passageway indicated by the numeral 160 through which the feeding tube passes, and a suction tube 30. The suction tube 30 opens into the VAC sponge as in embodiments of endoVAC devices described above and terminates in an external port 162 for connection to an external suction source, for application of a negative pressure to the wound via the peripheral side face 159 of the VAC sponge 14. In at least some embodiments, the suction tube 30 for the VAC sponge 14 may be an integral component of the feeding tube. In other embodiments, the VAC sponge and its suction tube 30 may be mounted to the feeding tube.

Another embodiment of a vacuum sponge device 164 is shown in FIGS. 25A, 25B, and 25C. In this instance, the VAC sponge 14 is in the form of a mat with a suction tube 30 disposed in an end margin 166 of the mat. A plurality of through openings 168 are provided along the region of the suction tube within the mat for application of the negative pressure to the mat in use. A fastening system in the form of hook tape 170 of the general type used in Velcro™ type fastening systems is affixed to the "internal" face of an opposite end region 172 of the mat 14 to the end margin 166. In order to mount the mat in position on a feeding tube (e.g., 158) or other insertion tube to be inserted through the wound in the skin of the subject, the tube is laid on the end margin 166 of the mat and the mat is wrapped tightly about the tube as illustrated in FIGS. 25A, 25B, and 25C. Fastening of the mat 14 is achieved by engagement of the hook tape with the exposed sponge material on the opposite "outer" face of the mat (see FIG. 25C). An illustration of a vacuum sponge device 164 in position within a wound 174 through skin 176 is shown in FIG. 26 in which the proximal end of feeding tube 158 extends through fascia tissue 178 into the lumen of the bowel 180 (e.g., stomach) and the balloon 160 is in an inflated condition. When a device of the type shown in FIGS. 25A, 25B, and 25C and FIG. 26 is in position, a clear or other suitable adhesive tape or covering is placed over the wound about the feeding tube 158 (or other insertion tube) to secure the device in position and to seal the outer end of the rolled mat 14 from the atmosphere for application of suction to the wound by the mat via the suction tube 30 of the device.

The VAC sponge 14/mat in at least some embodiments may be slid along the relevant insertion tube into the wound following placement of the insertion tube through the wound. Accordingly, the VAC sponge or mat 14 may be retro-mounted on an existing or pre-inserted drain or other insertion tube, and slid down into position in the wound for treatment of the wound.

The location of the VAC sponge/mat 14 of a vacuum assisted device (e.g., 156, 164) within a wound in the skin through which the feeding or other insertion tube extends as described herein may provide desirable outcome(s) such as one or more of managing fluid(s) that may otherwise leak from the wound, draw wound tissue together, enhance or speed the wound healing process, slow or avoid worsening of existing tissue exoriation or erosion of wound tissue, and avoid, manage or reduce oedema in the wound tissue.

Typically, the suction applied to the sponge 14 of an endoVAC device embodied by the invention via a suction tube 30 will be greater than 5.5 mm Hg and generally, in a range of from 11 mm Hg to 140 mm Hg. Most typically, the suction applied to the sponge 14 is in a range of from 50-100 mm Hg although, different levels of suction may be utilised for different applications and endoVAC devices, the optimum level of suction being able to be determined by the attending medical physician or practitioner.

Devices as described herein will generally be retained in position and negative pressure applied to the relevant wound for 3 to 5 days while the wound heals. In embodiments in which a wound through the skin of a patient is treated, negative pressure treatment of the wound may continue for a longer period during which the VAC sponge 14 may be replaced one or more times.

Besides the large bowel, an endoVAC device embodied by the invention may, for example, be utilised to assist healing of fistula, and fallopian, upper gastrointestinal (G.I tract), tracheal, bronchial, oesophagus, esophagogastric, gastrojeuneal and pancreatojejunal wounds as indicated above such as following esophagectomy or bariatric surgery. Indeed, the endoluminal surface can be any G.I tract or other endoluminal surface amenable to treatment with a device as described herein. Moreover, besides wounds resulting from resection of tissue, a device as described herein has application to assisted healing of wounds resulting from, but not limited to, ulcers, trauma, radiotherapy, radiofrequency ablation, ethanol ablation, cryosurgery, chemotherapy, and polypectomies. Hence, the term "wound" as used herein is to be taken in its broadest context to encompass wounds inflicted by surgery and medical treatments, trauma caused by accidents, and wounds resulting from physiological diseases or conditions (e.g., a fistula).

Various types of VAC sponge 14 suitable for use in a device of the invention are known, non-limiting examples of which may include open cell polyurethane and polyvinyl alcohol foamed plastics with or without a reticulated cell structure. The pores of the sponge may be in a range of from about 100 µM to about 1000 µM, more usually in a range of from about 200 µM to 600 µM and generally, in a range of from about 400 µM to 600 µM. Desirably, the foamed plastics material employed is essentially non-adherent to the wound. Alternatively, the device can be removed from the patient before any deleterious adherence to the wound or tissue ingrowth into the sponge 14 occurs. In other embodiments of a device in accordance with the invention, the absorbent material from which the porous element 14 and/or the further absorbent element(s) (e.g., 70 and/or 80) are formed may be a suitable gauze or wadding (e.g., conventionally used for treating wounds).

An endoVAC device embodied by the invention can be provided using readily available materials. For example, when the patient is a member of the porcine family, a cylindrical tube of open pore sponge can be cut lengthwise and tubing (e.g., French size 16 or 18; Bard Medical, Covington, GA, USA) sutured in position within the sponge to provide the suction tube 30. Further such tubing forming the drainage tube 22 is then placed in the sponge such that it extends beyond the proximal end of the sponge and sutured in position in the sponge and to secure it to the suction tube. The sponge is then sutured longitudinally closed over both tubes enclosing them within, and impervious tape is wrapped about the sponge to seal the exposed proximal and distal ends of the sponge. Foamed plastics material suitable for use as a sponge 14 and/or the further absorbent element 70 and/or 80 of an embodiment of a device of the present invention is commercially available (e.g., GranuFoam™ sponge; Kinetic Concepts, Inc., San Antonio, TX, USA).

Employing a device in accordance with the invention may, in one or more embodiments, allow for a colostomy or ileostomy associated with surgery of the large bowel such as for CRC (e.g., Lower Anterior Resection (LAR)), and the risk of anastomotic leakage connected with subsequent reversal of the colostomy or ileostomy, to be avoided. Likewise, by facilitating the healing of anastomotic wound, the risk of leakage and/or infection of the wound may be decreased. To further facilitate healing, in at least some embodiments, the VAC sponge or other porous element 14 may be impregnated or coated with drugs or other therapeutic agents such as antibiotics for release at, or application to, the wound site. For instance, a silver ion releasing antimicrobial coating may be applied to the peripheral outer face of the sponge for application to the wound.

Whilst various embodiments have been described above, it will be understood that numerous various and modifications can be made without departing from the invention. For example, embodiments may be provided in which the expandable element 34 is a stent (e.g., a wire or other suitable stent) that is in a collapsed state when the device is being located in position within the patient and is operably arranged to be expanded to press the outer sponge 14 into contact with the wound and surrounding endoluminal surface in use. The stent will normally be enclosed in an expandable plastic or other covering sealing the stent from the sponge. Any suitable such stent can be employed. In addition, the internal diameter of the drainage tube 22 can be greater than that of the particular embodiments shown in the accompanying figures which follow and as such, the relative dimensions and proportions of an endoVAC device embodied by the invention can vary and are not limited to those of the currently exemplified embodiments.

Accordingly, the above described embodiments are merely illustrative and not restrictive.

The invention claimed is:

1. A device for applying a negative pressure to a wound opening through the skin to the exterior of the body of a patient, wherein the wound further opens into an underlying internal lumen of the patient through an opening in a surrounding wall defining the lumen, the device comprising:

an insertion tube for being inserted into the wound through the opening of the wound in the skin;

a flexible porous element for being inserted into the wound such that the porous element is pressed against the wound around the insertion tube for application of the negative pressure to the wound in use via a peripheral outer face of the porous element between opposite proximal and distal ends of the porous element; and a suction tube for being connected to a suction source externally of the patient's body and which is in fluid communication with the porous element to apply the negative pressure to the porous element with operation of the suction source, the porous element being mounted on the insertion tube and the insertion tube being for extending from the porous element to protrude externally from the wound opening in the skin;

wherein the insertion tube is for extending from the wound into the internal lumen when the insertion tube is located in position in the wound, the insertion tube comprising a balloon for being inflated in the lumen to anchor the insertion tube in position in the wound, and the balloon being mounted on the insertion tube forwardly of the porous element.

2. The device according to claim 1, wherein of the proximal and distal ends of the porous element at least one is sealed against egress of bodily substances of the patient into the porous element.

3. The device according to claim 1, wherein at least the proximal end of the porous element is sealed against egress of the bodily substances into the porous element.

4. The device according to claim 1, wherein the insertion tube passes through the porous element.

5. The device according to claim 1, wherein the porous element is in the form of a mat for being wrapped around the insertion tube.

6. The device according to claim 5, further comprising a fastening system for fastening the mat when wrapped around the tube to retain the mat in a wrapped condition.

7. The device according to claim 1, wherein the insertion tube is a drain or feeding tube.

8. The device according to claim 1, wherein the insertion tube is a feeding tube.

9. The device according to claim 1, wherein the porous element is fabricated from an absorbent material.

10. The device according to claim 9, wherein the porous element is a sponge.

11. The device according to claim 1, wherein both the proximal and the distal end of the porous element are sealed against egress of bodily substances of the patient into the porous element.

12. The device according to claim 1, wherein the insertion tube is other than a drain tube.

13. The device according to claim 1, wherein the porous element is slidable along the insertion tube.

14. The device according to claim 1, wherein the porous element is retro-mounted to the insertion tube.

15. A method for treating a wound about an insertion tube passing through the wound into an underlying internal lumen of the patient, the wound opening to exterior of the body of the patient through the skin of the patient, and the method comprising:

locating a flexible porous element mounted on the insertion tube into the wound whereby the insertion tube protrudes externally from the wound opening in the skin and extends from the wound into the lumen through an opening in a surrounding wall defining the lumen, and the porous element has a peripheral outer face defined between opposite proximal and distal ends of the porous element, the porous element being in fluid communication with a suction source externally of the patient's body for application of a negative pressure to the wound around the insertion tube via the peripheral outer face of the porous element with operation of the suction source, and wherein the insertion tube comprises a balloon for being inflated in the lumen to anchor the insertion tube in position in the wound, and the balloon is located on the insertion tube forwardly of the porous element;

inflating the balloon in the lumen to anchor the insertion tube in position in the wound; and applying the negative pressure to the wound via the peripheral outer face of the porous element.

16. The method according to claim 15, wherein the insertion tube passes through the porous element.

17. The method according to claim 15, wherein the porous element is located into the wound by being slid along the insertion tube.

18. The method according to claim 15, wherein the porous element is mounted to the insertion tube whilst the insertion tube is in the lumen of the patient.

19. The method according to claim 15, comprising wrapping the porous element about the insertion tube to mount the porous element on the insertion tube, and fastening the porous element to retain the porous element on the insertion tube in a wrapped condition.

20. The method according to claim 19, wherein the porous element is in the form of a mat.

21. The method according to claim 15, wherein the porous element is fabricated from an absorbent material.

22. The method according to claim 15, wherein the porous element is a sponge.

23. The method according to claim 15, further comprising retro-mounting the porous element in position on the insertion tube.

* * * * *